(12) United States Patent
Zhan

(10) Patent No.: US 8,248,599 B2
(45) Date of Patent: Aug. 21, 2012

(54) METHODS OF POLARIZATION ENGINEERING AND THEIR APPLICATIONS

(75) Inventor: Qiwen Zhan, Mason, OH (US)

(73) Assignee: University of Dayton, Dayton, OH (US)

( * ) Notice: Subject to any disclaimer, the term of this patent is extended or adjusted under 35 U.S.C. 154(b) by 696 days.

(21) Appl. No.: 12/305,731

(22) PCT Filed: Jun. 21, 2007

(86) PCT No.: PCT/US2007/014480
§ 371 (c)(1),
(2), (4) Date: Mar. 13, 2009

(87) PCT Pub. No.: WO2007/149534
PCT Pub. Date: Dec. 27, 2007

(65) Prior Publication Data
US 2010/0141939 A1    Jun. 10, 2010

Related U.S. Application Data

(60) Provisional application No. 60/805,370, filed on Jun. 21, 2006.

(51) Int. Cl.
*G01J 3/44* (2006.01)
(52) U.S. Cl. ...................................................... 356/301
(58) Field of Classification Search .................. 356/301; 850/30–32
See application file for complete search history.

(56) References Cited

U.S. PATENT DOCUMENTS

| | | | |
|---|---|---|---|
| 4,947,034 A | 8/1990 | Wickramasinghe et al. | |
| 5,044,723 A | 9/1991 | MacDonald | |
| 5,286,971 A | 2/1994 | Betzig et al. | |
| 5,361,314 A | * 11/1994 | Kopelman et al. | ............ 359/368 |
| 5,499,313 A | 3/1996 | Kleinerman | |
| 5,559,330 A | 9/1996 | Murashita | |
| 5,602,820 A | 2/1997 | Wickramasinghe et al. | |

(Continued)

FOREIGN PATENT DOCUMENTS
WO    02068919 A1    9/2002
(Continued)

OTHER PUBLICATIONS

Janunts et al., "Excitation and superfocusing of surface plasmon polaritons on a silver-coated optical fiber tip", Apr. 20, 2005, Optical Communications, #253, pp. 118-124.*

(Continued)

*Primary Examiner* — Kara E Geisel
(74) *Attorney, Agent, or Firm* — Dinsmore & Shohl LLP

(57) ABSTRACT

Special polarization states are generated that have unique focusing properties that may be used to create extremely strong longitudinal fields. Combined with surface plasmon excitation, these polarization states can be used in apertureless near-field scanning optical microscopy systems. A radially polarized beam is directed into a plasmon-generating optical fiber comprising a metal coated, tapered, apertureless tip. The apertureless tip excites surface plasmon waves and direct the surface plasmon waves to the tip when a radially polarized beam propagates along the plasmon-generating optical fiber. An objective lens collects the near field optical signals from a sample positioned adjacent to the apertureless. Potential spatial resolution of the apertureless NSOM could reach beyond 10 nm. Such strong field enhancement allows the development of a reliable nano-Raman system that can measure mechanical as well as chemical compositions of samples with resolution beyond 10 nm.

19 Claims, 15 Drawing Sheets

U.S. PATENT DOCUMENTS

| | | | |
|---|---|---|---|
| 5,641,896 A * | 6/1997 | Karrai | 850/7 |
| 5,664,036 A | 9/1997 | Islam | |
| 5,960,147 A | 9/1999 | Muramatsu et al. | |
| 6,370,306 B1 | 4/2002 | Sato et al. | |
| 6,408,123 B1 | 6/2002 | Kuroda et al. | |
| 6,795,630 B2 | 9/2004 | Challener et al. | |
| 6,944,380 B1 | 9/2005 | Hideo et al. | |
| 7,048,732 B2 | 5/2006 | Ellingsen | |
| 7,106,935 B2 | 9/2006 | Challener | |
| 7,142,306 B2 | 11/2006 | Wu et al. | |
| 2003/0039429 A1 | 2/2003 | Inoue et al. | |
| 2007/0018082 A1 | 1/2007 | Ohtsu et al. | |

FOREIGN PATENT DOCUMENTS

| | | |
|---|---|---|
| WO | 2004003932 A2 | 1/2004 |

OTHER PUBLICATIONS

Bouhelier et al., "Plasmon-coupled tip-enhanced near-field optical microscopy", Jun. 2003, Journal of Microscopy, vol. 210, pp. 220-224.*

Hayazawa et al., "Detection and characterization of longitudinal field for tip-enhanced Raman spectroscopy", American Institute of Physics, Applied Physics Letters, vol. 85, No. 25, Dec. 20, 2004, p. 6239-6241.

Jia et al., "Direct measurement of a radially polarized focused evanescent field facilitated by a single LCD", Optics Express, vol. 13, No. 18, Sep. 5, 2005.

Kurihara et al., "Fiber-optic conical microsensors for surface plasmon resonance using chemically etched single-mode fiber", Science Direct, Analytica Chimica Acta 523 (2004) 165-170.

Ayars et al., "Fundamental differences bet3ween micro- and nano-Ramon spectroscopy", Journal of Microscopy, vol. 202, Pt 1, Apr. 2001, pp. 142-147.

Descrovi, "Longitudinally polarized fields in near-field imaging systems", Aug. 2005.

Inouye et al., "Near-field scanning optical microscope using a metallized cantilever tip for nanospectroscopy", Part of the SPIE Conference on Near-Field Optics: Physics, Devices and Information Processing, SPIE vol. 3791, Jul. 1999.

Chen et al., "Numerical study of an apertureless near field scanning optical microscope probe under radial polarization illumination", Optics Express, vol. 15, No. 7, Apr. 2, 2007, pp. 4107-4111.

Mehtani et al., "Optical properties and enhancement factors of the tips for apertureless near-field optics", Institute of Physics Publishing, J. Opt. A: Pure Appl. Opt. 8, Feb. 8, 2006, pp. S183-S190.

Tortora, "Optical Properties of Nano-Structured Materials Studied by Means of Interferometric Techniques", Sep. 2005.

Aeschimann et al., "Polarization Contrast in Cantilevered Probe-Based Near-Field Optical Microscopy".

Qiwen Zhan, "Properties of circularly polarized vortex beams", Optics Letters, vol. 31, No. 7, Apr. 1, 2006, pp. 867-869.

* cited by examiner

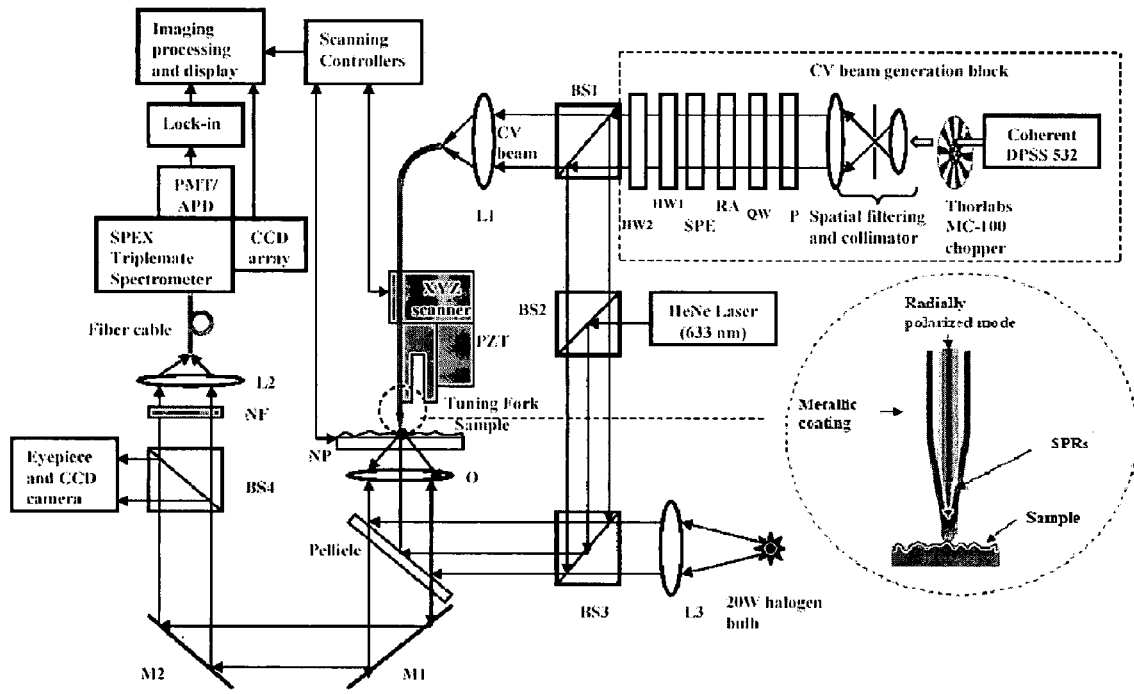

P: polarizer; QW: quarter-wave plate; RA: radial analyzer; SPE: spiral phase element; HW1, HW2: half-wave plates; L1, L2 and L3: lenses; BS1, BS2, BS3 and BS4: beamsplitters; M1 and M2: mirrors; O: infinity corrected objective lens; NP: low profile nano positioner; NF: Semrock holographic notch filter; SPEX: SPEX Triplemate 0.6 meter spectrometer; PMT: photomultiplier; APD: PerkinElmer SPCM-AQR-15 single photon avalanche photodiode; CCD array: Andor iDUS cooled (-100 °C) CCD detector; Lock-in: SR530 analog lock-in amplifier. A Veeco ECU-plus unit with I/O-U board is used for the tuning-fork feedback as well as scanning controls. A Veeco I/O-P two channel photon counter board is attached to the imaging processing unit. A Nikon TE-2000U inverted microscope is used for mounting and sample scanning.

FIG. 16

METHODS OF POLARIZATION ENGINEERING AND THEIR APPLICATIONS

The present invention relates to methods of polarization engineering and their applications in optical near-field imaging.

Polarization is one of the fascinating properties of light. This vector nature of light and its interactions with matters enable many optical devices and provide greater freedom in optical system design. Polarization propagation and interaction with materials have been extensively explored in optical inspection and metrology, display technologies, data storage, optical communications, astronomy, as well as biological studies. Most past research dealt with spatially homogeneous states of polarization Special polarization states generated have unique focusing properties that may be used to create extremely strong longitudinal fields. By spatially arranging the polarization of a light beam purposefully and carefully, new effects that can expand the functionality and enhance the capability of optical systems can be expected. This type of engineered polarization can be called spatially inhomogeneous polarization or spatially variant polarization.

One example of the spatially inhomogeneous polarization is light with cylindrical symmetry in polarization as shown in FIG. 1. These so-called cylindrical vector (CV) beams are solutions of Maxwell's equations that obey cylindrical symmetry in both amplitude and phase. FIG. 1a illustrates radial polarization, FIG. 1b illustrates azimuthal polarization, and FIG. 1c illustrates generalized cylindrical polarization.

Bessel beams are other solutions to the Maxwell's equations that do not suffer diffractive spreading. These non-diffracting beams were first proposed by Durnin et al. Since the introduction of this concept, Bessel beams have been attracting continuous interest. Most of the work has dealt with propagating scalar Bessel beams. As Durnin et al pointed out, a wave with amplitude $U(r,z)=\exp(ik_z z)J_0(k_r r)$ where $J_0(k_r r)$ is the zeroth order Bessel function of the first kind, is a solution to the Helmoholtz equation. When the condition $k_r < nk_0$ is satisfied, non-diffracting beam that maintains its intensity distribution $J_0^2(k_r r)$ in all transverse planes along the propagation z-axis can be obtained. A propagating Bessel beam can be described by the superposition of a set of plane waves with wave vectors lying on a cone surface, which can be realized by an axicon type device. Evanescent Bessel beam solutions to the Maxwell's equations (with $k_r > nk_0$) have also been proposed and studied recently. Owing to required axial symmetry, propagating Bessel beams with radial polarization are typically used in combination with total internal reflection to generate such evanescent non-diffracting beams. Their applications as virtual tips in near-field optical microscope have been explored to avoid the stringent proximity requirements between the tip and sample. However, the geometry proposed was rather complicated and difficult to implement.

Therefore, there is a need for a simple set up for the generation of evanescent Bessel beams via surface plasmon excitation. This method utilizes radial polarization symmetry as well as the angular selectivity of surface plasmon resonance (SPR). The sensitivity and field enhancement offered by SPR make this technique an attractive approach for generating evanescent Bessel beams that can be used as virtual probe in near-field optical imaging and sensing applications.

The recent rapid progress in nanoscience and nanotechnology has been largely driven by the invention of new instruments that allow for the fabrication, measurement and manipulation of structures at the nanometer scale. Optical techniques are inherently nondestructive and have been widely used in materials diagnostics and characterizations. Owing to diffraction, normal optical imaging systems have difficulties resolving features with sub-wavelength lateral dimensions. Near-field optical techniques, such as near-field scanning optical microscopy (NSOM), have been investigated to overcome this limit. NSOM is an optical technique capable of providing subwavelength resolving power and has found many applications in nanophotonics, biophotonics and materials diagnostics. The most common practice of this technique uses metallic-coated tapered fiber tip with a nano-aperture. The light transmits through this nano-aperture and excites the sample locally. It is the confinement of the nano-aperture that provides the resolving power far beyond the diffraction limit. However, the nano-aperture also gives rise to an extremely low light throughput ($\sim 10^{-6}$), which represents one significant drawback of this technique. Delicate fabrication procedure is required to produce the nano-aperture on the tip and improve the throughput. These drawbacks limit the achievable spatial-resolution of nano-aperture NSOM to around 100 nm in practice.

Therefore, there is a need for an apertureless NSOM technique to overcome these drawbacks. In an apertureless NSOM, an extremely sharp dielectric, semiconductor, or metallic tip is used as a Rayleigh scattering probe. The radius of this apertureless probe can be made much smaller than an aperture probe, thus providing excellent spatial-resolution. A spatial-resolution of 1 nm can be achieved. In addition, if a metallic probe is used, the local excitation of surface plasmon at the probe tip provides a significant local field enhancement. This local field enhancement effect can be utilized in many applications such as single molecule detection, two-photon microscopy, and Raman spectroscopy, etc.

For many years Raman spectroscopy has been a powerful tool for the investigation of molecular vibrations and rotations. Raman scattering may be regarded as an inelastic collision of incident light with molecule of materials. The interaction between the incident light and the vibrational/rotational energy of the molecules cause a spectrum shift in the scattered light. Specific molecules have their own distinctive features or "fingerprints" in the spectrum shifts. By study the Raman shift, information about the chemical compositions of the sample can be identified. Materials micromechanical properties and local deformations also affect the shift. Thus, measuring the Raman shift image can provide a mapping of the stress/strain distribution in the sample. Traditional Raman spectroscopy techniques use laser beams with large footprint, which limited the achievable spatial resolution.

In order to obtain spatially resolved material properties, there is a need for a micro-Raman technique using high numerical aperture objective for application in materials diagnostics. Typical spatial resolution on the order of several microns can be achieved with micro-Raman technique. However, a much higher resolution is required to meet the challenges presented by the ever decreasing feature sizes of present nanomaterials and nanofabrication techniques. Realization of reliable nano-Raman measurements is considered as the "holy grail" in the Raman spectroscopy community. With the strong field enhancement of the apertureless NSOM, the Raman signal is significantly strengthened, enabling reliable comprehensive characterization of the nanomaterials.

According to the present invention, an optical system comprising a beam generating assembly, an optical microscope assembly, and a signal detection assembly is presented. The beam generating assembly comprises a laser source and is configured to convert laser output from the laser source into a radially polarized beam as input to the optical microscope assembly. The optical microscope assembly comprises a plasmon-generating probe set-up and an objective lens. The beam generating assembly is configured to direct the radially polarized beam into the plasmon-generating optical probe set-up of the optical microscope assembly. The plasmon-generating optical probe set-up comprises a metal coated, tapered, apertureless tip defining an apex. The tip may be built either by an optical fiber having a tapered end or by a cantilever (an atomic force microscope tip). The apertureless tip is configured to excite surface plasmon waves and direct the surface plasmon waves to the apex of the tip when a radially polarized beam propagates from the beam generating assembly in the direction of the apex of the tip. The objective lens is configured to collect near field optical signals from a sample positioned adjacent to the apex of the apertureless tip and direct the near field optical signals to the signal detection assembly.

In accordance with one embodiment of the present invention, focused polarized beams are injected into a metallic coated optical fiber tip to create a light source. This light source may then be utilized in apertureless near-field scanning optical microscopy (NSOM) and Raman spectroscopy applications.

In accordance with another embodiment of the present invention, evanescent Bessel beams are generated via surface plasmon excitation and used as virtual probe in near-field optical imaging and sensing applications.

In accordance with still another embodiment of the present invention, cylindrical vector and circularly polarized vortex beams are generated and focused.

Accordingly, it is a feature of the embodiments of the present invention to have a light source for use in apertureless near-field scanning optical microscopy (NSOM) and Raman spectroscopy.

It is another feature of the embodiments of the present invention to generate and focus a cylindrical vector (CV) beam.

It is still another feature of the embodiments of the present invention to generate and focus a circularly polarized vortex (CPV) beam.

It is yet another feature of the embodiments of the present invention to generate an evanescent Bessel beam. Other features of the embodiments of the present invention will be apparent in light of the description of the invention embodied herein.

The following detailed description of specific embodiments of the present invention can be best understood when read in conjunction with the following drawings, where like structure is indicated with like reference numerals and in which.

Figure 4:
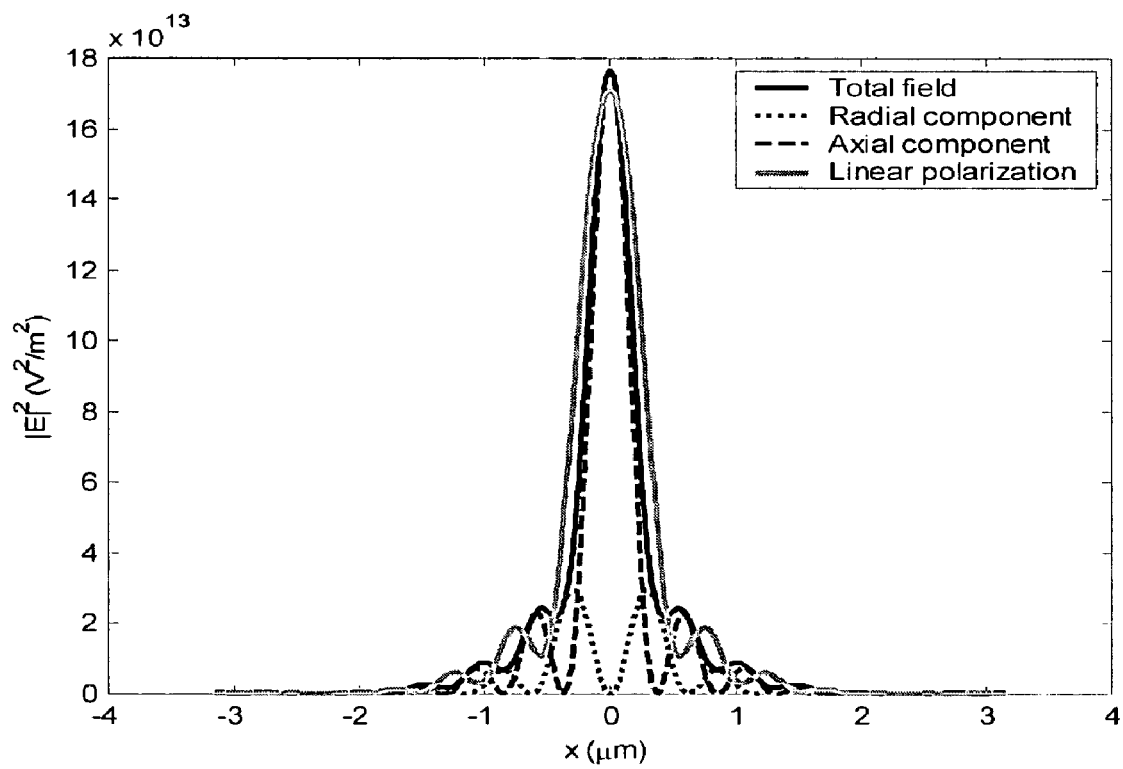

FIG. 4 graphs of field distribution at a particular numerical aperture according to an embodiment of the present invention.

Figure 5:
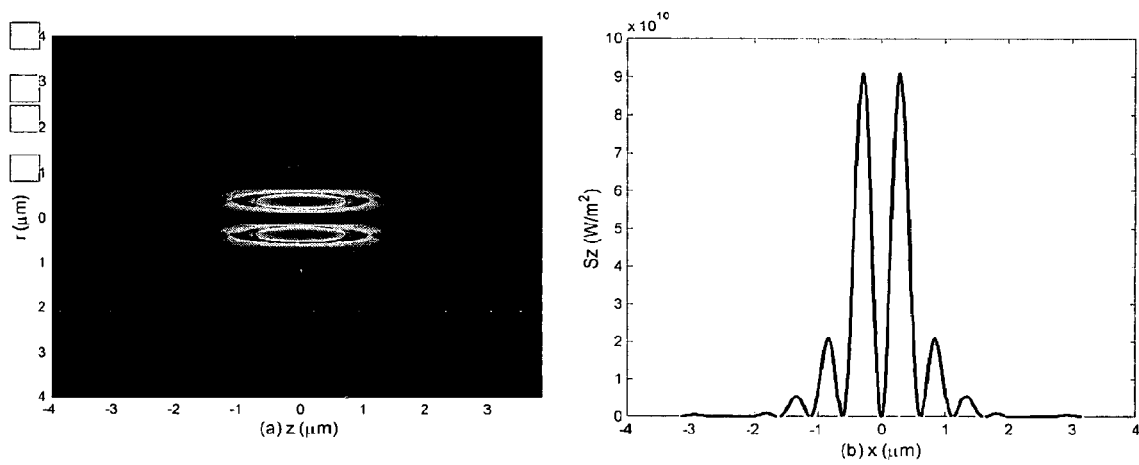

FIG. 5 graphs an axial component of a highly focused radial polarization according to an embodiment of the present invention.

Figure 6:
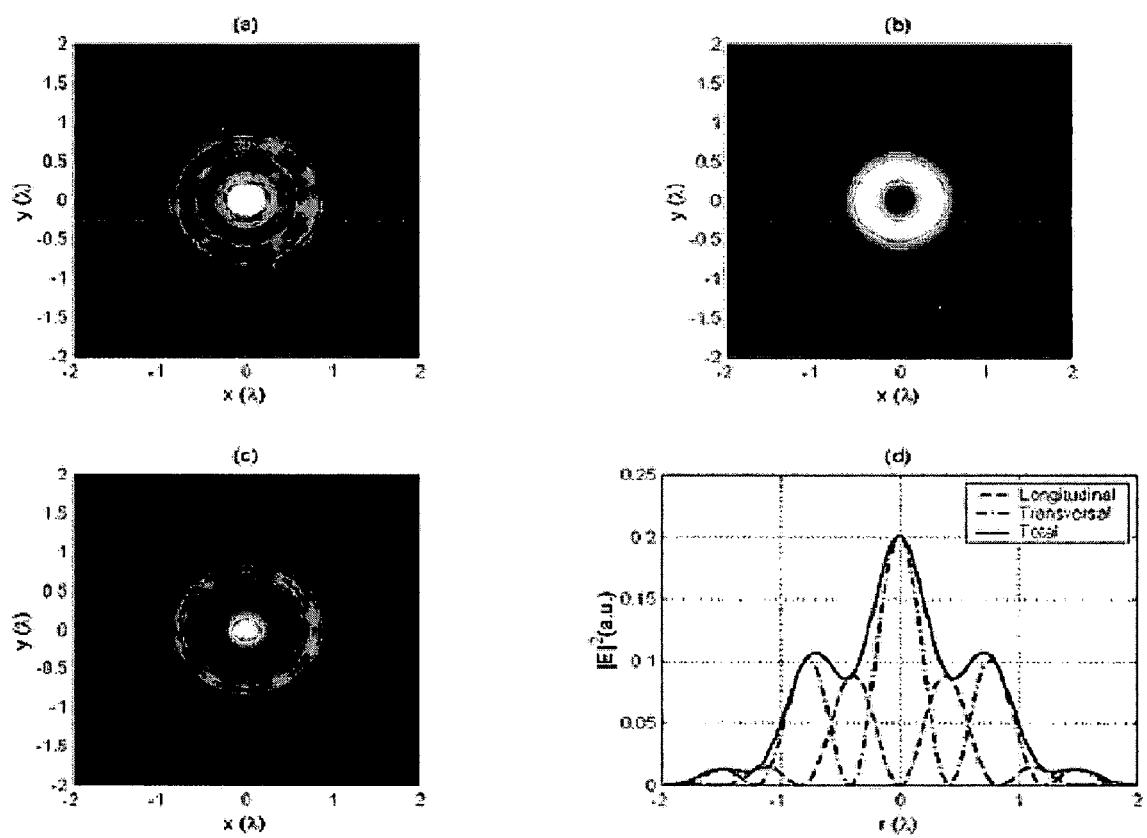

FIG. 6 illustrates the two-dimensional field distribution for a highly focused left-hand circularly polarized vortex beam with charge m=0 according to an embodiment of the present invention.

Figure 7:
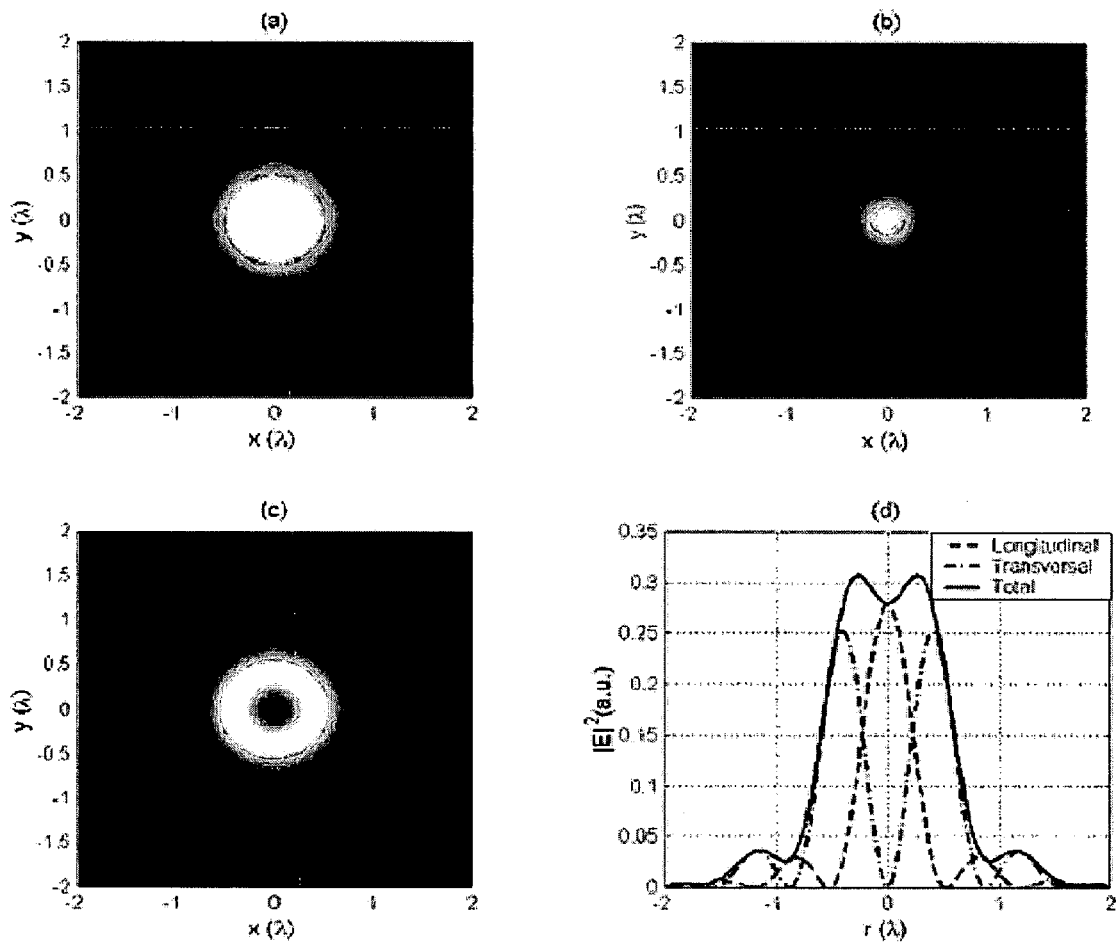

FIG. 7 illustrates the two-dimensional field distribution for a highly focused left-hand circularly polarized vortex beam with charge m=−1 according to an embodiment of the present invention.

Figure 8:
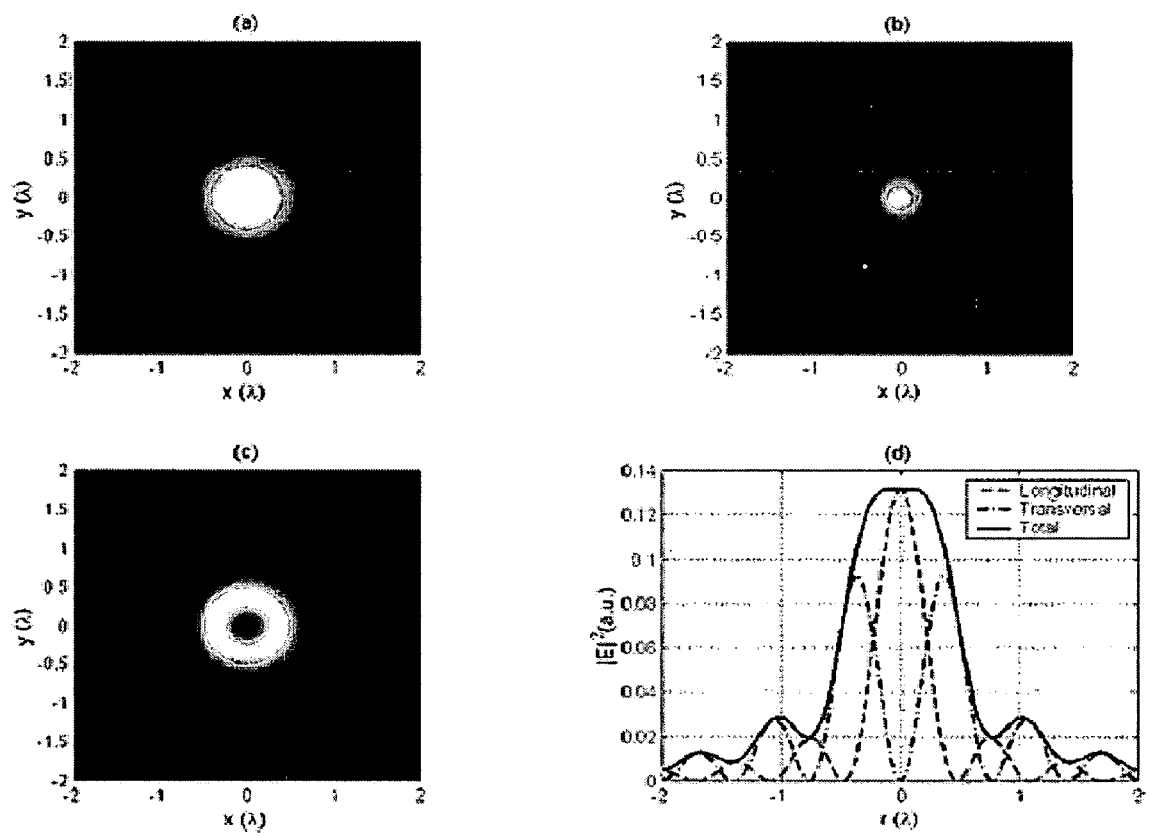

FIG. 8 illustrates flattop focusing with a highly focused left-hand circularly polarized vortex beam with charge m=−1 according to an embodiment of the present invention.

Figure 9:
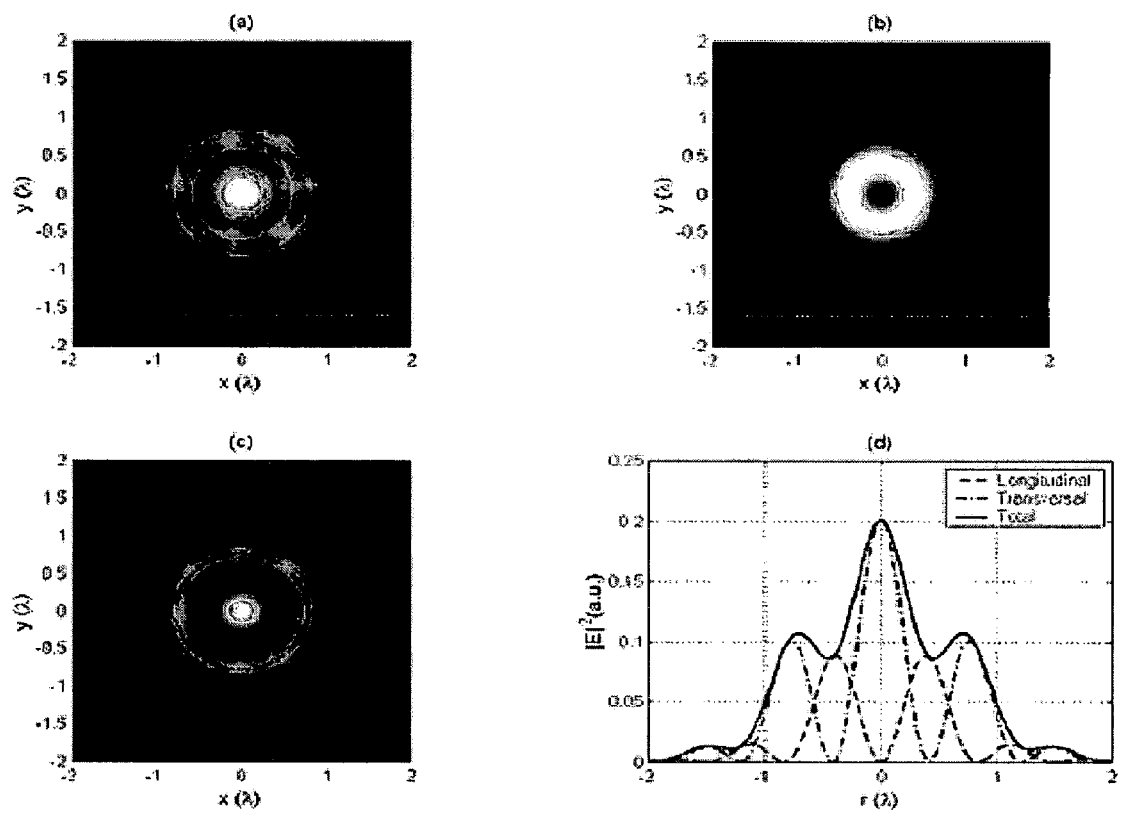

FIG. 9 illustrates the two-dimensional field distribution for a highly focused left-hand circularly polarized vortex beam with charge m=−2 according to an embodiment of the present invention.

Figure 10:
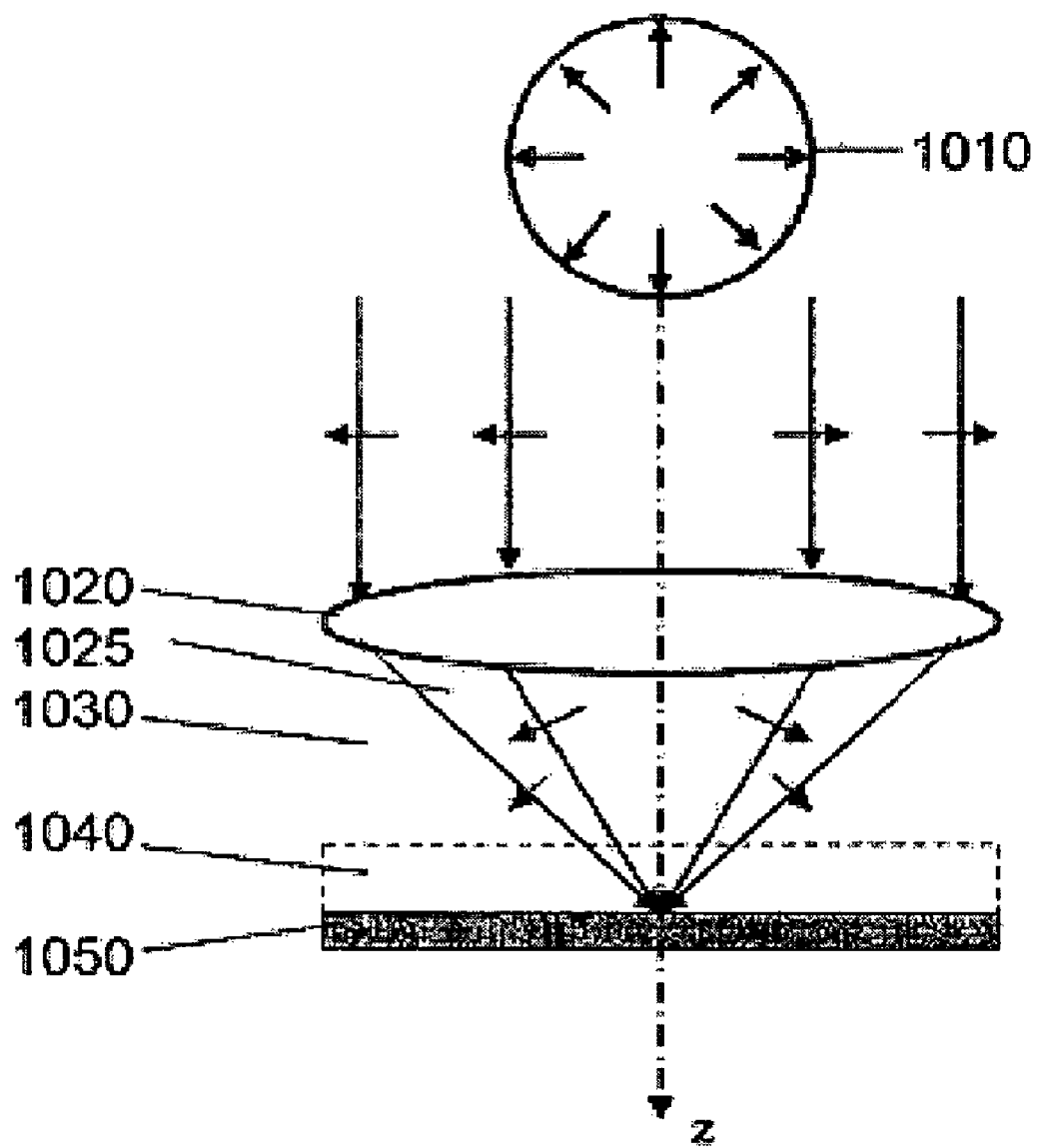

FIG. 10 illustrates setup for evanescent Bessel beam generation according to an embodiment of the present invention.

Figure 11:
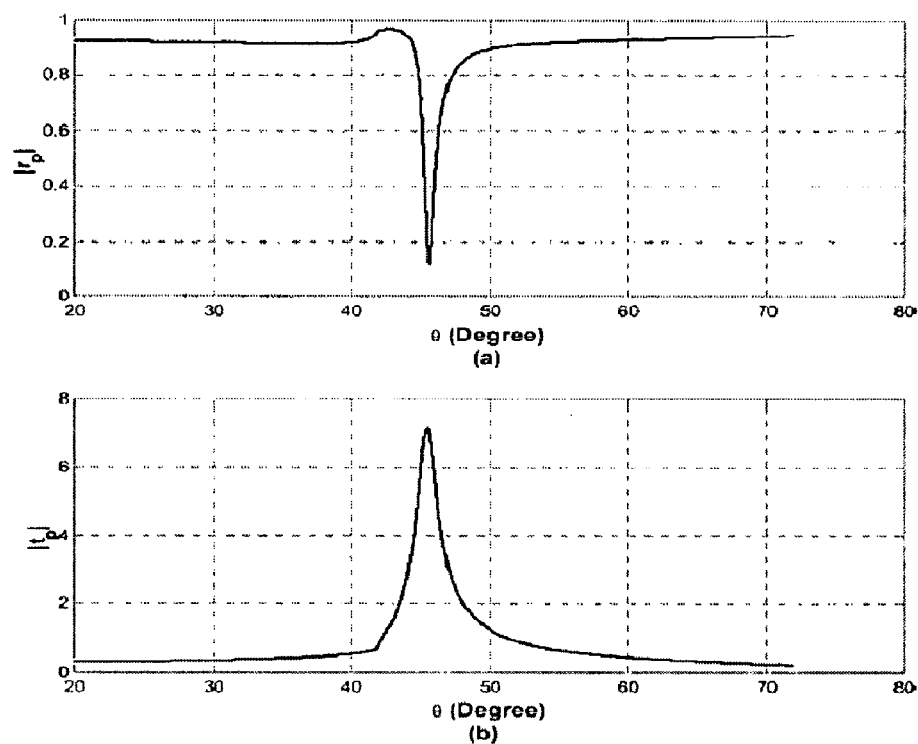

FIG. 11 illustrates calculated magnitude of the reflection and transmission coefficient versus incident angles for p-polarized light incident on the dielectric/metal interface according to an embodiment of the present invention.

Figure 12:
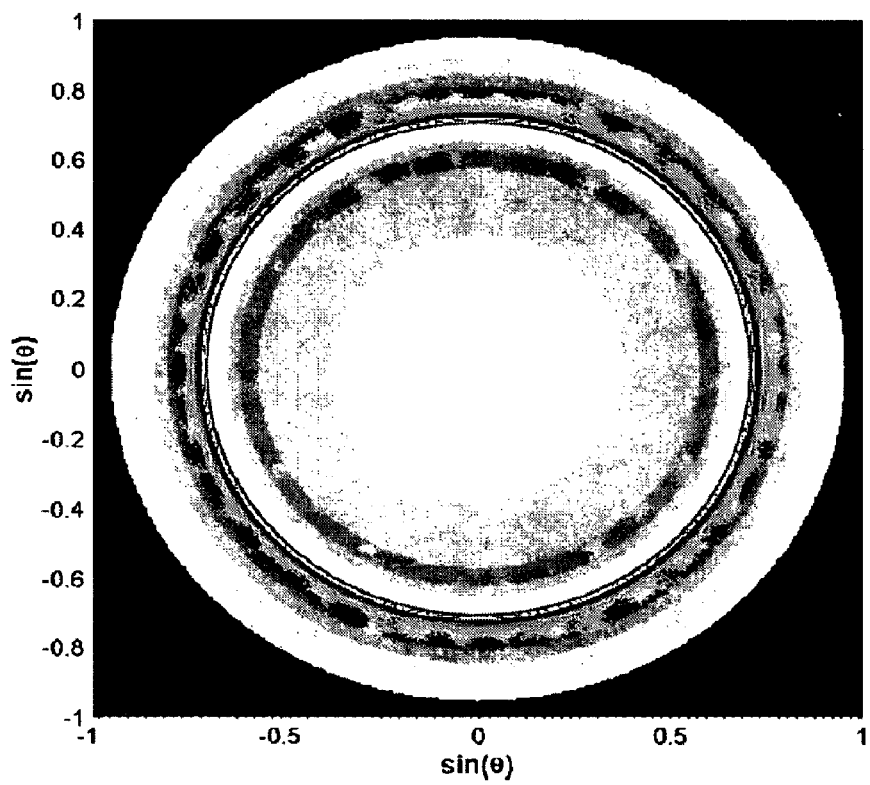

FIG. 12 illustrates simulated intensity distribution at the back focal plane of the objective lens after reflection according to an embodiment of the present invention.

Figure 13:
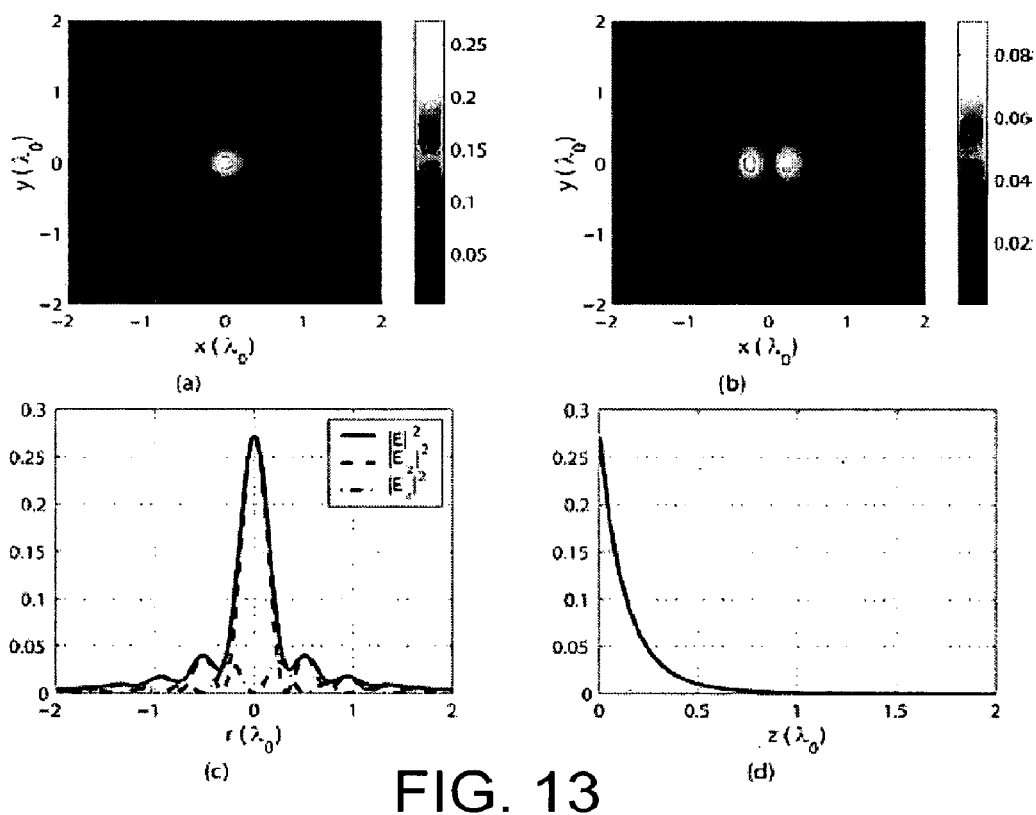

FIG. 13 illustrates numerical simulation results using vectorial diffraction theory according to an embodiment of the present invention.

Figure 14:
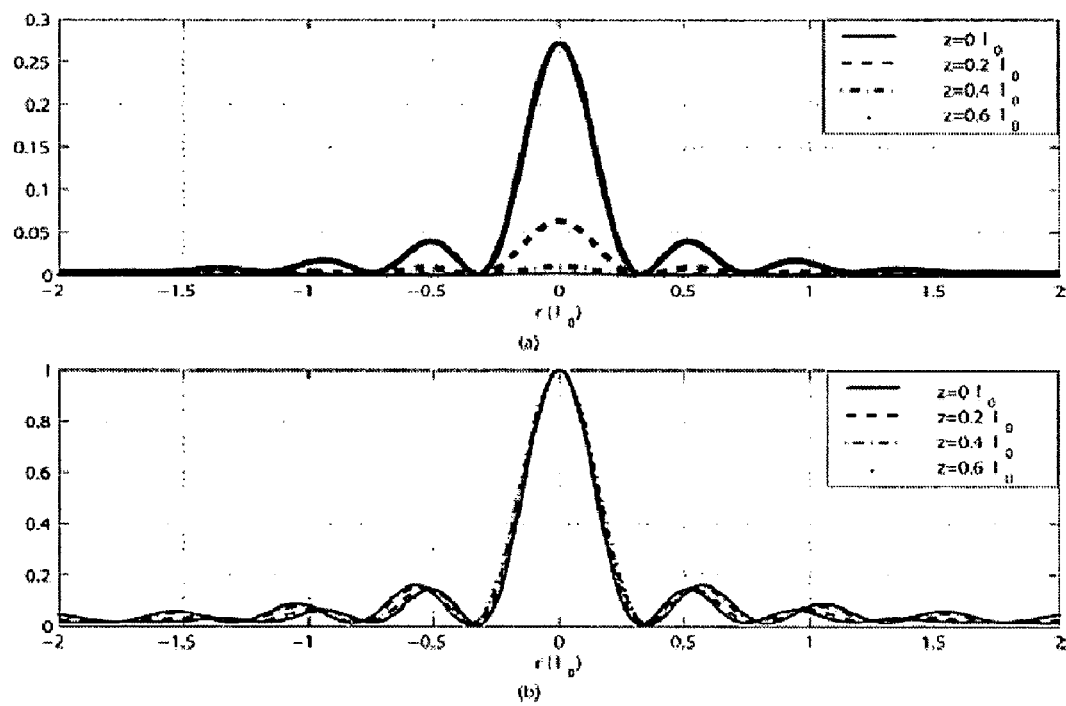

FIG. 14 illustrates the main lobe shape of the beam remains almost constant according to an embodiment of the present invention.

Figure 15:
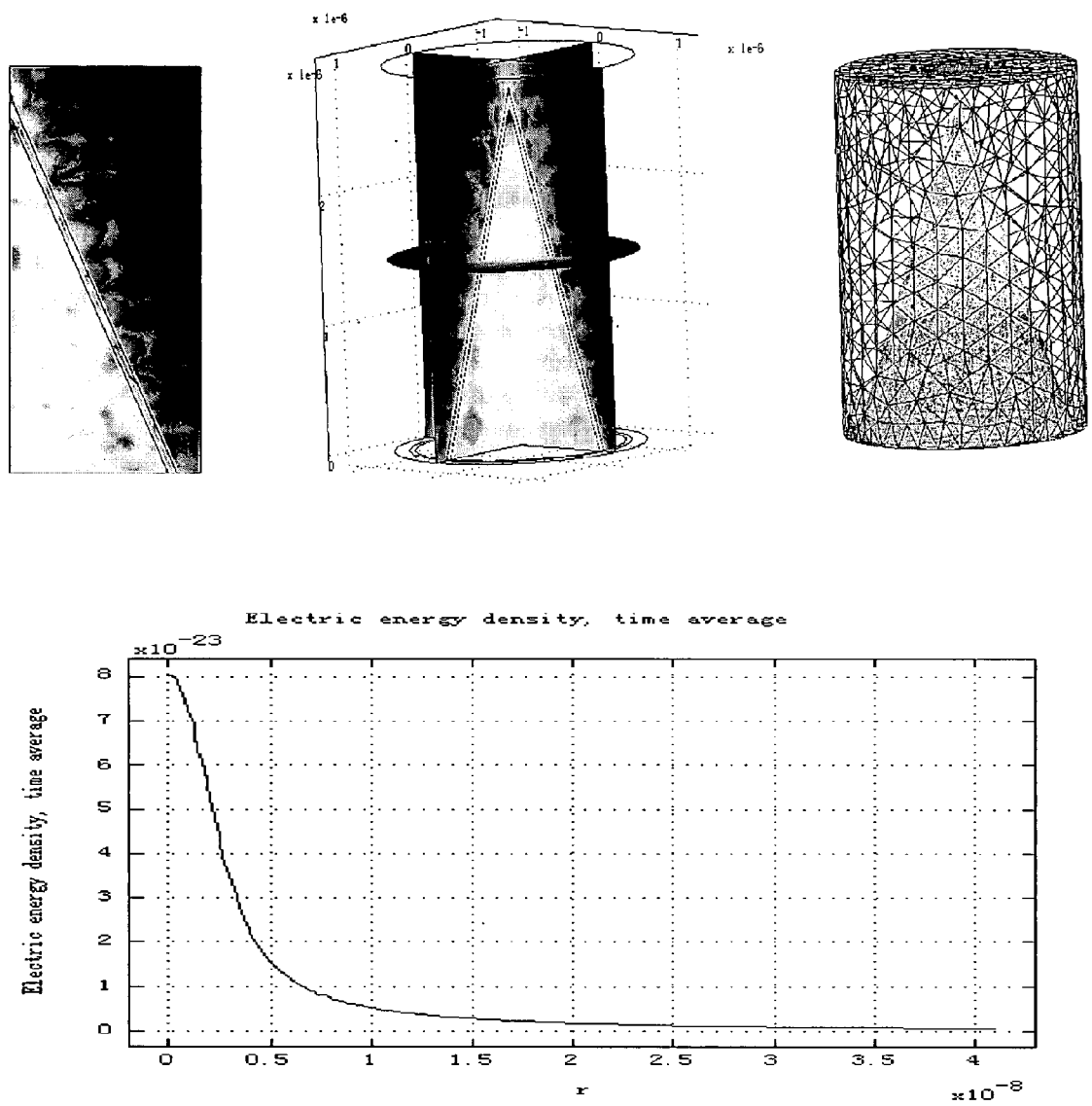

FIG. 15 illustrates finite element method simulation results according to an embodiment of the present invention.

FIG. 16 illustrates a tuning fork shear force apertureless near-field scanning optical microscopy according to an embodiment of the present invention.

Figure 17:
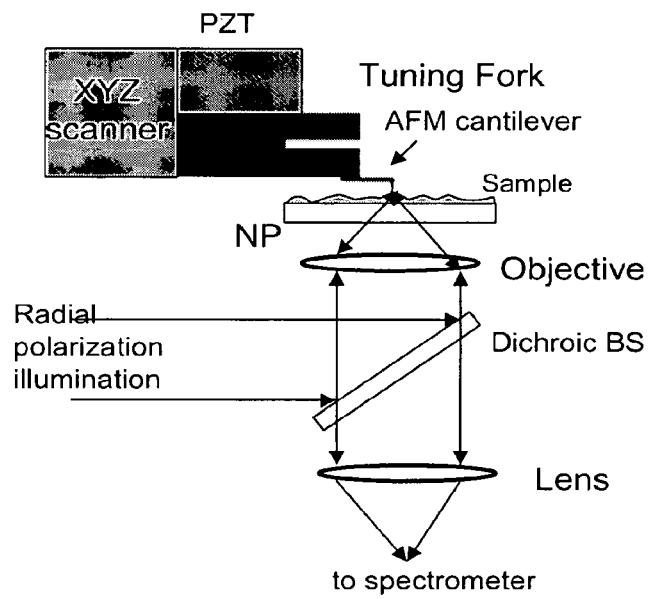

FIG. 17 illustrates normal force tuning fork apertureless near-field scanning optical microscopy with radial polarization excitation according to an embodiment of the present invention.

Figure 18:
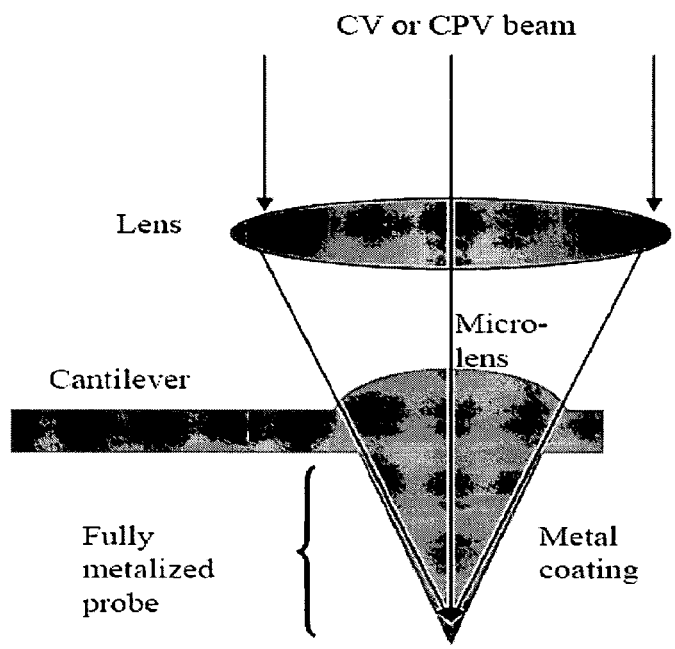

FIG. 18 illustrates an apertureless-near-field scanning optical microscopy probe with micro-lens according to an embodiment of the present invention.

Figure 19:
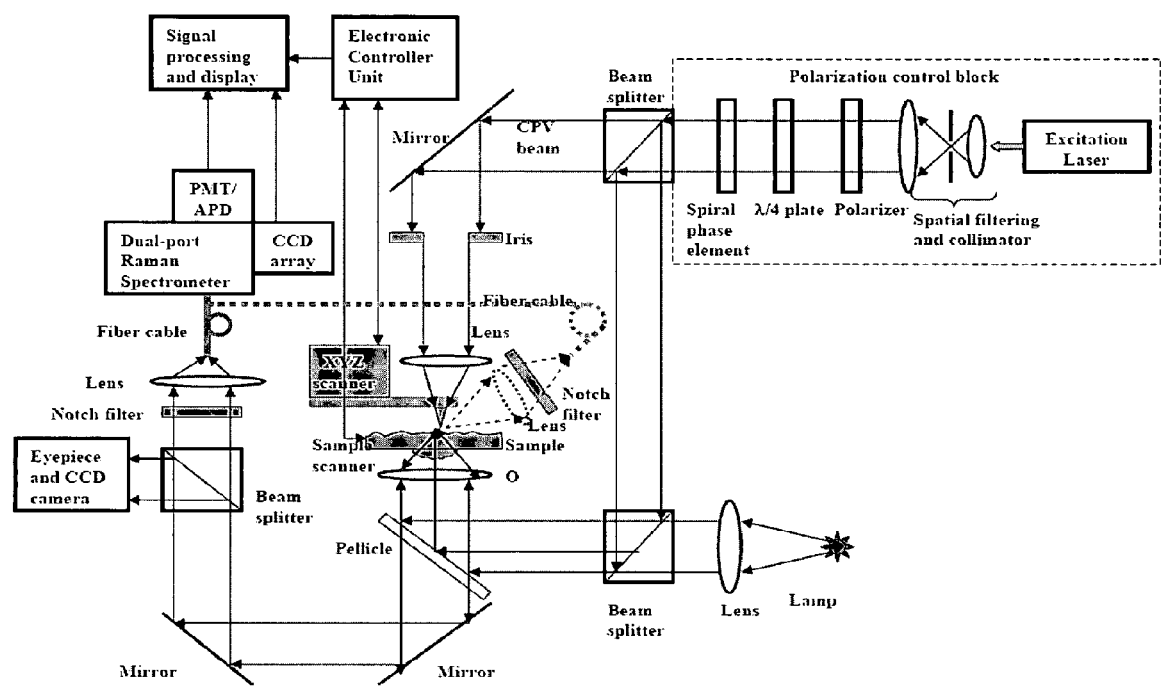

FIG. 19 diagrams an implementation of a nano-Raman system based on an apertureless near-field scanning optical microscopy according to an embodiment of the present invention.

In the following detailed description of the embodiments, reference is made to the accompanying drawings that form a part hereof, and in which are shown by way of illustration, and by way of limitation, specific embodiments in which the invention may be practiced. It is to be understood that other embodiments may be utilized and that logical, mechanical and electrical changes may be made without departing from the spirit and scope of the present invention.

Generate Cylindrical Polarization

Figure 1:
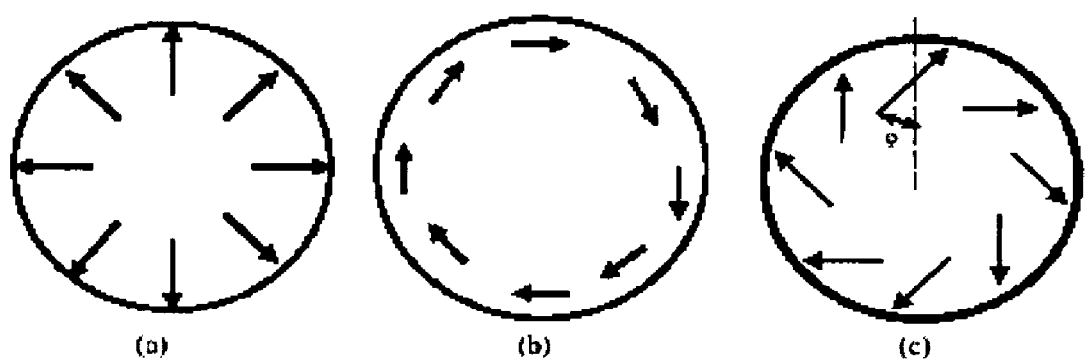
FIG. 1 illustrates examples of cylindrical vector beams.
Figure 2:
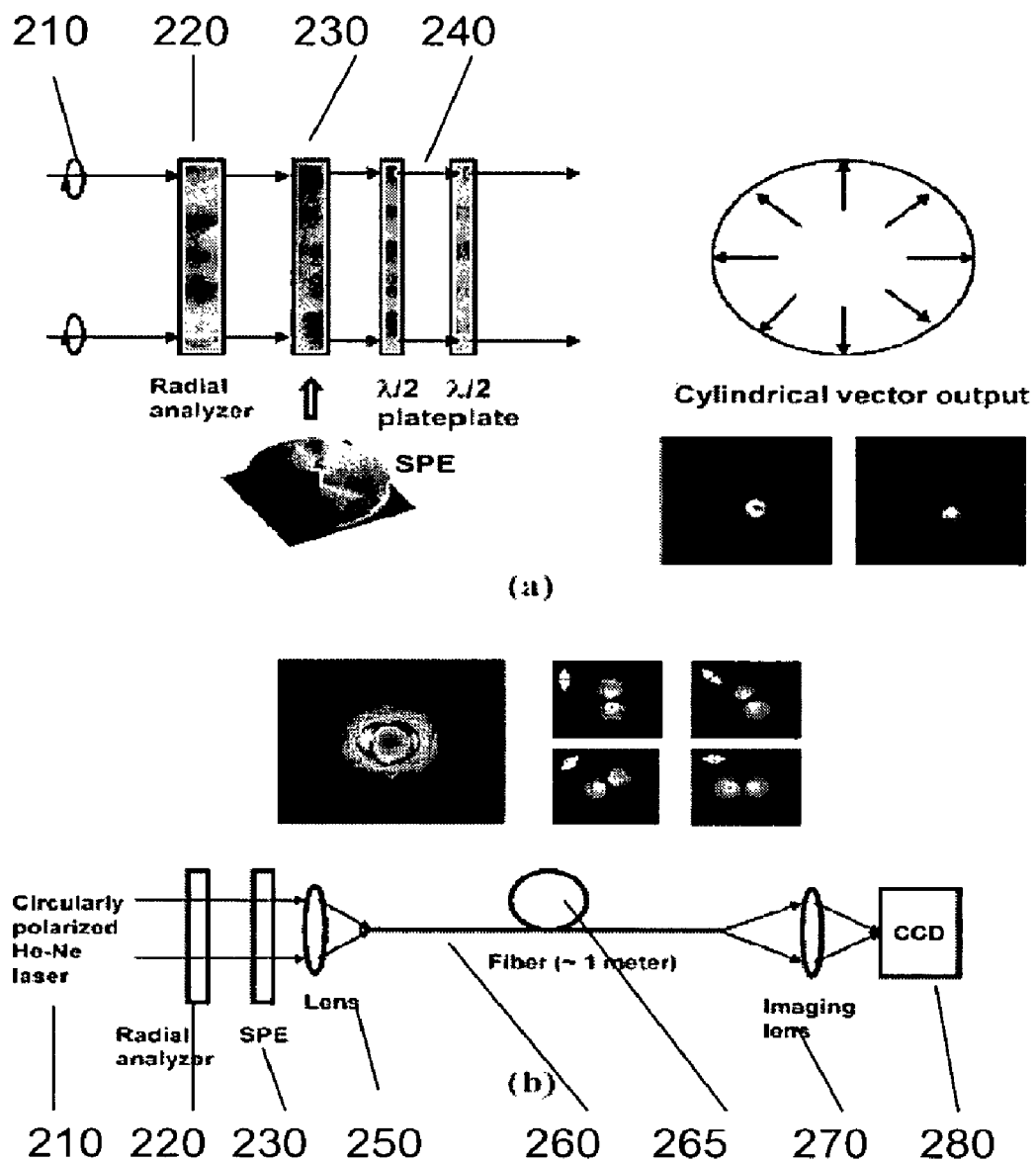
FIG. 2a illustrates cylindrical beam generation according to an embodiment of the present invention.
FIG. 2b illustrates experimental launching cylindrical vector beams into an optical fiber according to an embodiment of the present invention.

Referring initially to FIG. 2a, a circularly polarized laser beam 210 is used as the input to a radial analyzer 220. Simple cylindrical vector (CV) beam generation and manipulation techniques can be experimentally demonstrated using a radial analyzer 220. A radial analyzer 220 is a polarization device with a polarization transmission axis aligned along the radial directions. The field after the radial analyzer 220 ($E_{out}=e^{j\phi}e_r$) is radially polarized with an additional spiral Berry's phase. This helicity breaks the cylindrical symmetry in phase and needs to be compensated through inserting a spiral phase element (SPE) 230 with the inverse helicity in the setup. Such SPE 230 can be e-beam written or fabricated with other micro-fabrication techniques such as, for example, gray scale lithography or multiphoton polymerization process. It can also be realized with spatial light modulators (SLM). The phase delay of a SPE 230 must grow linearly with azimuthal angle. In order to generate CV beams, the phase delay should reach 360° with one full revolution. Fabricating an optic of this sort that is intended to be used in air and has high surface quality with a single-wavelength phase change around its perimeter is highly challenging; furthermore, such an optic will only have a single-wavelength phase change at a single wavelength. Therefore, SPEs 230 can be fabricated so that can be immersed in a near-index-matching (NIM) fluid.

Consider a SPE 230 comprised of a material with an index of refraction, $n_2$, immersed in a medium with an index of refraction, $n_1$, and with a total thickness of d. For this thickness to represent a full-wave delay, $\Delta n = n_2 - n_1 = \lambda/d$, where $\lambda$ is the wavelength of light employed. In other words, $d = \lambda/\Delta n$. Thus, for instance, if $\Delta n = 0.01$, then d can be 100λ and a surface roughness of 5λ is equivalent to a surface roughness of λ/20 for an optic that would be used in air. Thus, such an optic can be fabricated far more readily than one intended to be used in air. Note that $\Delta n$ can be tuned readily for any given wavelength by changing the composition of the NIM fluid. Furthermore, if the dispersion of the NIM fluid can be chosen such that $d = \lambda/\Delta n(\lambda)$ for a broad range of wavelengths, the optic will be effectively achromatic. It will certainly be possible to attain this goal over the bandwidth of an ultrafast laser pulse, and it will be possible to extend the operating range considerably farther with a well-chosen NIM fluid.

The SPEs 230 should be placed appropriately to compensate the Berry's phase after the radial analyzer 220. Such Berry's phase may have different sign ("+" or "−") topological charges, depending on the handness (left or right) of the incident circular polarization. Simply flipping the SPE 230 will switch the sign of the topological charge introduced by the SPE 230. Thus compensation of the Berry's phase can be achieved by correctly orient the SPE 230. A double half-wave-plate polarization rotator 240, emulating the function of a Faraday rotator, rotates the polarization to the desired cylindrically symmetric pattern. The polarization pattern was confirmed by observing the intensity pattern after a linear polarizer at different orientations. Far field patterns were observed to verify the generation of such a CV beam. Due to the cylindrical symmetry in polarization, the far field has a dark hollow center. Experimental results shown in the inset of FIG. 2(a) verify that cylindrical beams can be generated with this method.

Cylindrical polarization modes can also be directed into optical fiber. It is known that a multi-mode step index optical fiber can support the transverse-electrical ($TE_{01}$) and transverse-magnetic ($TM_{01}$) annular modes possessing cylindrical polarization symmetry, with the $TE_{01}$ mode being azimuthally polarized and the $TM_{01}$ mode being radially polarized. Under weakly-guiding approximation, these modes have the same cutoff parameter that is lower than all the other modes except the $HE_{11}$, fundamental mode. In general, it is difficult to excite these modes in a fiber without exciting the fundamental mode first. The presence of a strong fundamental mode would spoil the cylindrical polarization purity.

As shown in FIG. 2(b), the CV beams generated previously can be used to excite these modes in an optic fiber 260. A fiber 260 about one meter long was carefully chosen such that it only supports the fundamental mode and the annular modes. By performing the input polarization, the coupling into the fundamental mode is minimized and second order annular modes with high efficiency can be generated. A radially polarized mode is shown in the inset of FIG. 2(b). The polarization symmetry can be observed by inserting a polarizer 265 between the fiber 260 and the imaging lens 270. Intensity patterns for different polarizer orientations were recorded and demonstrated successfully launched the radially polarized mode in the fiber 260. Currently, the efficiency is around 10%. Thermal reflow process may be used to reduce the diffraction loss from the phase discontinuity of the SPE 230 and further improve the efficiency. Azimuthally polarized mode as well as hybrid mode were also excited by twisting the optical fiber 260. The torsion in optical fiber 260 induces a birefrigence in the fiber. It can be shown that the uniformaly twisted fiber behaves like a medium exhibiting rotatory power. Thus, it provides a convenient means of polarization control.

Generation of Circularly Polarized Vortex Beams

Besides the generation and manipulation of the CV beams, the connections between the CV beams and circularly polarized vortex (CPV) beams can be shown. Optical singularities have drawn much interest recently. These singularities occur at points or lines where the phase or the amplitude of field is undefined or changes abruptly. Most past research has been devoted to phase singularities in homogeneously polarized light wave (scalar singularities). One class of scalar singularities is the scalar vortex. A scalar vortex has a spiral phase wave front around a singularity point where the phase is undefined. Topological charge, $$l = \frac{1}{2\pi}\oint \nabla\phi \cdot d\vec{s},$$

is used to characterize a scalar vortex. Recently, vectorial vortices that involve disclinations have been studied for inhomogeneously polarized wave. Disclinations are points or lines of singularities in the patterns or directions of transverse vector field. One such example is the vectorial vortex for CV beams, which have polarization singularities at the center of the beam.

A CPV beam is a circularly polarized beam with spiral phase wave front. This type of beams can be generated by passing a circularly polarized light through a SPE as described above. In a cylindrical coordinate system, a left-hand circularly (LHC) polarized beam with planar wave-front can be expressed as:

$$\vec{E}_{LHC} = P(r)(\vec{e}_x + j\vec{e}_y)/\sqrt{2} = P(r)[(\cos\phi\vec{e}_r - \sin\phi\vec{e}_\phi) + j(\sin\phi\vec{e}_r + \cos\phi\vec{e}_\phi)]/\sqrt{2} = P(r)e^{j\phi}(\vec{e}_r + j\vec{e}_\phi)/\sqrt{2} \quad (1)$$

where P(r) is the axially symmetric amplitude distribution of the beam. For simplicity, the amplitude of unity for the beams is assumed, e.g. P(r)=1. Similarly, for a right-hand circular (RHC) polarization, $\vec{E}_{RHC} = P(r)(\vec{e}_x - j\vec{e}_y)/\sqrt{2} = P(r)e^{-j\phi}(\vec{e}_r - j\vec{e}_\phi)/\sqrt{2}$. If a LHC vortex beam with charge of m is considered, the field is $\vec{E} = e^{j(m+1)\phi}(\vec{e}_r + j\vec{e}_\phi)/\sqrt{2}$. It can be seen that a scalar vortex is decomposed into linear superposition of two vectorial vortices in the cylindrical polarization bases. The topological Pancharatnam charge is defined as $$l_{p,r} = \frac{1}{2\pi}\oint \nabla\phi_{p,r} \cdot d\vec{s} - 1,$$

where the Pancharatnam phase for radial polarization component is given by $\phi_{p,r} = \arg\langle E(r,\phi), E(r,0)\rangle = \arg[\cos\phi \cdot e^{j\phi}]$ and $l_{p,r}$ denotes the topological Pancharatnam charge. The topological Pancharatnam phase $\phi_{p,a}$ and charge for azimuthal polarization $l_{p,a}$ can be derived similarly. Then the total angular momentum in the direction of propagation per unit energy is given as:

$$J_z = \left[\frac{1}{2}(l_{p,r} + l_{p,a})\right] / \omega \qquad (2)$$

It appears that the total angular momentum in the direction of propagation per unit energy is given by the summation of the topological charge of the cylindrical polarization components, which apparently can not be done in the linear polarization bases. Another important point is that the helicity (±1 for circular polarization) is decomposed into the topological charges. This is most clearly shown by the left-hand circular polarization with charge of m=0. Thus, through the cylindrical bases decomposition, the connection between the helicity (spin-like photon properties) and the orbital angular momentum has been established. In the context of cylindrical polarization decomposition, helicity is no different from orbital angular momentum contribution, unless the interaction is with only a fraction of the beam cross section. Total angular momentum of optical beam can be calculated using simple algebraic addition and subtraction of topological Pancharatnam charge of the radial and azimuthal components, which is apparently different from the angular momentum properties of electrons.

Generation of Extremely Strong Longitudinal Field

CV beams are extensively studied for its focusing properties. Focusing laser beams into optimal spots is an interesting research topic that has many applications. It has been shown that one can create ultrasmall focal spot, focus with extended depth of focus, focus with flattop profile and optical-chain using radial polarization, one special case of cylindrical polarization. In many of these applications, a very strong longitudinal field component (i.e., electric field pointing along the propagation direction) is required and plays critical role. The generation of such strong longitudinal field for the CV beams generated in previous section can be shown. The focusing properties of circularly polarized vortex beams are studied and show that, with proper combination of the handness of the circular polarization and the charges of the phase singularity, it is possible to achieve focusing properties that are similar to those of the radial polarization.

Focusing Properties of CV Beams

There is an increasing interest in laser beams with radial polarization. Particular interest has been given to the high numerical aperture (NA) focusing properties of these beams and their applications as high-resolution probes. Due to the polarization symmetry, the electric field at the focus of a radially polarized beam has an extremely strong axial component, and the transverse size of the axial component is much smaller than that of the transversal component. This property may find applications in high-resolution microscopy, microlithography, metrology and nonlinear optics, etc.

Figure 3:
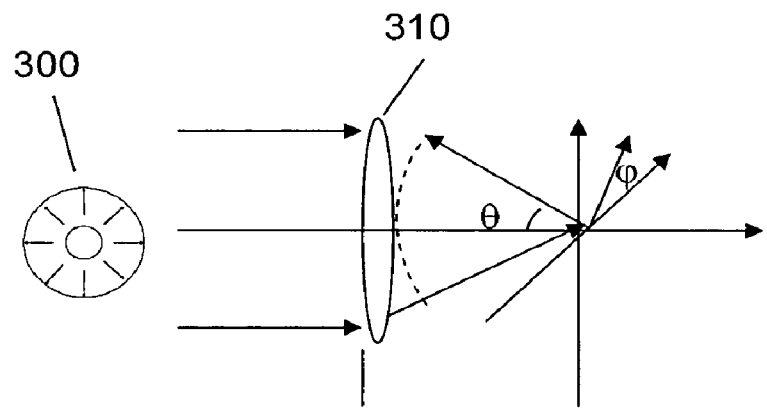
FIG. 3 illustrates the geometry for the creation of radial polarization according to an embodiment of the present invention.

The field distribution near the focus of highly focused polarized beams is analyzed with the Richards-Wolf vectorial diffraction method The geometry of the problem is shown in FIG. 3. The illumination is a radially polarized beam 300 with a planar wavefront over the pupil. An aplanatic lens 310 produces a converging spherical wave towards the focus of the lens. The particle to be trapped is assumed to be immersed in an ambience with refractive index of $n_1$. For simplicity, the refractive index on the object side is assumed to be the same as the ambience. The focal field can be written as $$\vec{E}(r,\phi,z) = E_r \vec{e}_r + E_z \vec{e}_z \qquad (3)$$

where $\vec{e}_r, \vec{e}_z$ are the unit vectors along the radial and axial directions. The amplitudes of two orthogonal components $E_r$, $E_z$ can be expressed as $$E_r(r, \varphi, z) = 2A \int_0^{\theta_{max}} \cos^{1/2}(\theta) P(\theta) \sin\theta \cos\theta J_1(kr\sin\theta) e^{ik_1 z\cos\theta} d\theta \qquad (4)$$

$$E_z(r, \varphi, z) = i2A \int_0^{\theta_{max}} \cos^{1/2}(\theta) P(\theta) \sin^2\theta J_0(kr\sin\theta) e^{ik_1 z\cos\theta} d\theta \qquad (5)$$

where $\theta_{max}$ is the maximal angle given by the NA of the objective lens, $P(\theta)$ is the pupil apodization function, $k_1$ is the wave number in the ambient medium, $J_n(x)$ is the Bessel function of the first kind with order n, and $A = n_1 \pi f/\lambda$ with f being the focal length. For many applications, such as high resolution imaging, it is sufficient to simply calculate the relative strength of each field components. However, quantitative estimation of the radiation forces requires the calculation of absolute field strength with given beam parameters. In the calculations, $\lambda = 1.047$ μm, $n_1 = 1.33$ and a simple annulus pupil apodization function were chosen $$P(\theta) = \begin{cases} P_0 & \text{if } \sin^{-1}(NA_1) \le \theta \le \sin^{-1}(NA/n_1) \\ 0 & \text{otherwise} \end{cases} \qquad (6)$$

where $P_0$ is a constant amplitude factor and NA is the lens numerical aperture determined by the outer radius of the annulus and $n_1$. The NA is chosen to be $0.95 n_1$. $NA_1$ corresponds to the inner radius of the annulus which is variable. The laser beam power is assumed to be 100 mW. As $NA_1$ is varied, the amplitude $P_0$ is adjusted accordingly to maintain the power level. As one example, field distribution for $NA_1 = 0.6$ is shown in FIG. 4. FIG. 4 shows a line scan of calculated focal plane energy distribution for a highly focused radial polarization.

From FIG. 4, it can be seen that the overall distribution of field strength is dominated by the axial component, giving a more compact focus. For comparison, the result for the linearly polarized incident is also shown. Thus, focused radial polarization provides stronger gradient force to pull the metallic particles towards the center of the focus. Another important feature of such a focal field is that the strong axial component is a non-propagating field and does not contribute to the energy flow along the propagation direction. Consequently, the time averaged Poynting vector $<S>_z = \text{Re}\{(\vec{E} \times \vec{H}^*)_z\}/2 = \text{Re}\{E_r H^*_\phi\}/2$ along the optical axis has a null at center. To demonstrate this, the corresponding time averaged Poynting vector is calculated and its axial component is shown in FIG. 5. FIG. 5(a) shows the two-dimensional distribution near focus and FIG. 5(b) shows the line scan of (a) at the focal point. The magnetic field is calculated in a similar way to that of the electric field calculation; assuming the magnetic field at the pupil plane is aligned along the azimuthal direction. From FIG. 5, it is clear that axial Poynting vector near optical axis is substantially zero. This has important meaning for metallic particle trapping in optical tweezers.

Focusing of Circularly Polarized Vortex Beams

The focusing properties of the circularly polarized vortex beams using the same focusing setup are examined. For example, the focal field distribution for left-hand circularly polarized vortex beam with charge of m can be derived using Richards-Wolf vectorial diffraction model and Bessel identities:

$$E_\rho(\rho_s, \phi_s, z) = A e^{j(m+1)\phi_s} j^{m+1} \int_0^\alpha \cos^{1/2}(\theta)\sin\theta\cos\theta \quad (7)$$
$$P_0(\theta)[J_{m+2}(k\rho_s\sin\theta) + j^{-2(m+1)}J_{-m}(k\rho_s\sin\theta)]e^{jkz_s\cos\theta}d\theta$$

$$E_z(\rho_s, \phi_s, z) = A e^{j(m+1)\phi_s} j^m \int_0^\alpha \cos^{1/2}(\theta)\sin^2\theta \quad (8)$$
$$P_0(\theta)[J_{m+1}(k\rho_s\sin\theta) + j^{-2(m+1)}J_{-(m+1)}(k\rho_s\sin\theta)]e^{jkz_s\cos\theta}d\theta$$

$$E_\phi(\rho_s, \phi_s, z) = -A e^{j(m+1)\phi_s} j^m \int_0^\alpha \cos^{1/2}(\theta)\sin\theta \quad (9)$$
$$P_0(\theta)[J_{m+2}(k\rho_s\sin\theta) + j^{-2(m+1)}J_{-m}(k\rho_s\sin\theta)]e^{jkz_s\cos\theta}d\theta$$

where $\alpha$ is given by NA=$\sin\alpha$, A is a constant related to the focal length and wavelength, $J_m(x)$ is the Bessel function of the first kind with order m. For scalar vortex that neglecting polarization, the field is always zero at the center of focus as long as the topological charge m≠0. It is different for the circularly polarized vortex beams. In order to have non-zero on-axis field strength at the focal plan, at least one of the Bessel functions in equations (7)-(9) needs to be the $0^{th}$ order. Otherwise, the total field will be zero at the center of the focus. From equations (7)-(9), it is clear that this occurs for m=0, −1, −2. For m=0, this is the trivial case for circular polarization. The equations for the focal fields are reduced to the Debye integral results. One of such example is shown in FIG. 6. FIG. 6 illustrates the calculated two-dimensional distribution of $|E|^2$ for a highly focused left-hand circularly polarized vortex beam with a charge, m=0. FIG. 6(a) shows the total field, FIG. 6(b) shows the longitudinal component $|E_z|^2$, FIG. 6(c) shows the transversal component $|E_t|^2$, and FIG. 6(d) shows the line scan of the focus. As shown in FIG. 6, the focus is dominated by the transversal field. As expected, the focus of left-hand circular polarization has a non-zero on-axis field due to the transversal field component.

If the beam is a LHC scalar vortex beam with charge of m=−1, then the expression for the left-hand circularly polarized vortex beam becomes $\vec{E}=(\vec{e}_r+j\vec{e}_\phi)/\sqrt{2}$, which is merely a linear superposition of the radial and azimuthal polarization. The radially polarized component is of particular interest due to its demonstrated unique focusing properties. When focused with high NA objective lens, the radial component contributes to a strong longitudinal focal field, with a surrounding donut focal field created by the azimuthal component (see FIG. 7). FIG. 7 illustrates the calculated two-dimensional distribution of $|E|^2$ for a highly focused left-hand circularly polarized vortex beam with a charge, m=−1. FIG. 7(a) shows the total field, FIG. 7(b) shows the longitudinal component $|E_z|^2$, FIG. 7(c) shows the transversal component $|E_t|^2$, and FIG. 7(d) shows the line scan of the focus. As shown in FIG. 7, a strong longitudinal field is generated by the radial component of the vortex beam. In order to ensure such a unique longitudinal field to occur, the handness of the circular polarization and the charge must be chosen carefully.

If right-hand circular polarization is used, a charge of m=+1 would be necessary to achieve this strong longitudinal field. More interestingly, flattop focus for the m=−1 case can be achieved simply through adjusting the illumination pupil aperture. One of such results is shown in FIG. 8. FIG. 8 illustrates flattop focusing with a highly focused left-hand circularly polarized vortex beam with a charge, m=−1. FIG. 8(a) shows the total field, FIG. 8(b) shows the longitudinal component $|E_z|^2$, FIG. 8(c) shows the transversal component $|E_t|^2$, and FIG. 8(d) shows the line scan of the focus showing that flattop focus can be obtained. This flattop condition is achieved by blocking 75.6% of the center of the objective lens pupil aperture.

For LHC scalar vortex beam with charge of m=−2, the field becomes $\vec{E}=e^{-j\phi}(\vec{e}_r+j\vec{e}_\phi)/\sqrt{2}$. This is almost identical with the expression for RHC in cylindrical polarization bases, except that the azimuthal component is π out-of-phase. Thus it is clear that the focal field strength should be identical to that of a focused RHC, which should also be identical to the results for LHC shown in FIG. 6. FIG. 9 illustrates the calculated two-dimensional distribution of $|E|^2$ for a highly focused left-hand circularly polarized vortex beam with a charge, m=−2. FIG. 9(a) shows the total field, FIG. 9(b) shows the longitudinal component $|E_z|^2$, FIG. 9(c) shows the transversal component $|E_t|^2$, and FIG. 9(d) shows the line scan of the focus. It can be seen that the field strength distribution in FIG. 9 is identical to that of FIG. 6. Another similarity between this beam and RHC is that they have equal total angular momentum density, which is −ℏ per photon. This leads to another point of interest which is the angular momentum of optical beams.

The focusing properties of these beams may have applications in high spatial-resolution imaging, photolithography, materials processing and characterization, and optical tweezers. Particularly, for those applications that utilize the strong longitudinal components, the circularly polarized vortex beam can be used as a simpler alternative.

Applications to Virtual Tips

A proposed setup for the generation of evanescent Bessel beams is shown in FIG. 10. A radially polarized beam 1010 illuminating the pupil plane of an aplanatic lens 1020 (NA=0.95) produces a converging spherical wave 1025 towards a dielectric/metal substrate 1040 interface located at the focal plane. A solid or liquid immersion material 1030 is used to match the index of refraction of the dielectric substrate 1040. In one embodiment, the refractive indices of the immersion material 1030 and the substrate 1040 are chosen to be $n_1$=1.5. A wavelength of $\lambda_0$=488 nm is used throughout. A 50 nm thin metal film 1050 of silver (∈=−7.9+0.736i at 488 nm) is deposited on the bottom of the dielectric substrate 1040. The medium below the silver layer is chosen to be air with $n_2$=1. For the strongly focused radially polarized illumination, the entire beam is p-polarized with respect to this multilayer interface.

As shown in FIG. 11, refection (FIG. 11(a)) and transmission (FIG. 11(b)) coefficient curves versus incident angles for p-polarized light incident on the dielectric/metal interface are calculated for this interface. It can be seen that surface plasmon resonance (SPR) condition is satisfied at $\theta_{sp}$=45.45°. FIG. 12 illustrates the simulated intensity distribution at the back focal plane of the objective lens after reflection. Due to the radial symmetry in this setup, the SPR excitation corresponds to a dark ring in the back focal plane of the objective lens.

The electric field in the vicinity of the focus can be calculated with the Richards-Wolf vectorial diffraction theory. The field components in the medium below the silver layer can be expressed as:

$$E_r(r, \varphi, z) = \quad (10)$$
$$2A \int_0^{\theta_{max}} \cos^{1/2}(\theta)P(\theta)t_p(\theta)\sin\theta\cos\theta J_1(k_1 r\sin\theta)e^{iz\sqrt{k_2^2-k_1^2\sin^2\theta}}d\theta$$

$$E_z(r, \varphi, z) = \qquad (11)$$
$$i2A \int_0^{\theta_{max}} \cos^{1/2}(\theta) P(\theta) t_p(\theta) \sin^2\theta J_0(k_1 r\sin\theta) e^{iz\sqrt{k_2^2 - k_1^2 \sin^2\theta}} \, d\theta$$

where $t_p(\theta)$ is the transmission coefficient for p-polarization at incident angle of $\theta$, A is a constant, $P(\theta)$ is the pupil apodization function, $J_m(x)$ is the $m^{th}$ order Bessel function of the first kind, $\theta_{max} = \sin^{-1}(NA)$ is given by the numerical aperture (NA) of the objective lens, $k_1$ and $k_2$ are the wave vectors in the medium that is above and below the silver layer, respectively. From results shown in FIG. 12, it can be seen that the SPR excitation performs an angular filter function for the transmitted field similar to that of an axicon. To illustrate the effect of this angular filter, the transmission curve is approximated with a delta function $t_p(\theta) = t_p(\theta_{sp})\delta(\theta - \theta_{sp})$, given the very narrow angular width for the SPR excitation. Then equations (1) and (2) are reduced to:

$$E_r(r, \varphi, z) = 2A\cos^{1/2}(\theta_{sp}) P(\theta_{sp}) t_p(\theta_{sp}) \sin(\theta_{sp}) \cos(\theta_{sp}) \qquad (12)$$
$$J_1(k_1 r\sin\theta_{sp}) e^{iz\sqrt{k_2^2 - k_1^2 \sin^2\theta_{sp}}}$$

$$E_z(r, \varphi, z) = \qquad (13)$$
$$i2A\cos^{1/2}(\theta_{sp}) P(\theta_{sp}) t_p(\theta_{sp}) \sin^2(\theta_{sp}) J_0(kr\sin\theta_{sp}) e^{iz\sqrt{k_2^2 - k_1^2 \sin^2\theta_{sp}}}$$

Under the SPR condition, $k_2^2 - k_1^2 \sin^2\theta_{sp} < 0$, thus clearly both the radial and longitudinal components become evanescent along the z-direction. In addition, both components maintain their transverse profiles. For the longitudinal component, it is an evanescent Bessel beam of the zeroth order, whereas the transversal component is an evanescent Bessel beam wave of the first order (donut shape). Evanescent Bessel beams can thus be generated with this rather simple setup.

Numerical simulations using the vectorial diffraction model given by equations (10) and (11) are shown in FIG. 13. In order to emphasize the evanescent nature, the central part of the illumination corresponding to angular portion below the critical angle $\theta_c = \sin^{-1}(n_2/n_1) \approx 41.8°$ is blocked. FIG. 13(a) shows the field strength $|E|^2$ of the evanescent Bessel beam generated at the bottom of silver layer. A nice and homogeneous spot is generated with the radial polarized illumination. In contrary, the same field distribution would be inhomogeneous and much weaker if a linear polarization illumination is used (shown in FIG. 13(b)), making it unsuitable for imaging and sensing applications. The field strength transverse profiles are illustrated in FIG. 13(c). It can be seen that there are two components contributing to the total field: radial component and longitudinal component. The longitudinal component is much stronger and dominates the total field distribution. From the transverse profile, the full-width-half-maximum (FWHM) spot size of the main lobe is calculated to be about $0.343\lambda_0$. For the longitudinal components, the FWHM is about $0.303\lambda_0$. The evanescent delay nature of the beam is shown in FIG. 13(d) with the propagation distance estimated at about $0.285\lambda_0$ by finding the $1/e^2$ point along the z-axis. The field strength transverse profiles at different distances from the silver layer are plotted in FIG. 14(a). To illustrate the non-diffracting property, normalized transverse profiles at these distances are also plotted in FIG. 14(b). One can see that all the main lobes almost overlap with each other, indicating that an evanescent Bessel beam can indeed be generated with the proposed simple setup. The slight deviation in the main lobe shape is attributed to the finite angular width for the SPR excitation.

It is well known that SPR excitation is very sensitive to its environment and may provide strong field enhancement, making it attractive for near-field optical imaging and sensing applications. Virtual probes using SPR has been proposed and studied. The evanescent Bessel beams generated with the proposed method is an excellent candidate for virtual probe that can alleviate the proximity requirement (within a few tens of nanometers typically) of many other near-field optical probes while providing reasonable spatial resolution, especially when the field enhancement property is utilized in nonlinear near-field optical imaging. For example, if two-photon imaging is considered, the FWHM will be $0.219\lambda_0$. If a wavelength of 300 nm illumination is used for silver thin film, this could provide a spatial resolution around 66 nm, which would be sufficient for many biomedical imaging and semiconductor metrology applications.

Thus, a simple method for the generation of evanescent Bessel beam is presented. When a radially polarized beam is strongly focused onto a dielectric/metal interface, surface plasmon waves are excited. The excitation of SPR mimics the function of an axicon. Consequently, evanescent Bessel beams are generated after the metal thin film. The sensitivity and field enhancement of SPR make the non-diffracting evanescent wave ideal virtual tip for near-field optical imaging and sensing. It is also worthy to point out that, in lieu of radial polarization, circularly polarized vortex beam with appropriate combination of handness and topological charges can also be used as a simpler alternative for the illumination.

In general, the effective NA of the virtual tips generated with such setup will be slightly above 1 due to the surface plasmon resonance conditions. This will limit the smallest achievable spot size (spatial resolution). In Order to generate even smaller spot size, one may replace the metal layer with a multilayer dielectric materials stack. Examples of these stack included the 1D photonic band gap structures (PBG) described by Haus et al. Using this type of 1D PBG stacks with appropriate incident and exit media, one can achieve very large field enhancement effect for TM polarized light and make sure the field in the exit medium is evanescent. Effective NA can be increased to much higher than 1. Combining with radial polarized illumination, an extremely confined and enhanced evanescent Bessel beam can be generated. In addition, the 1D PBG structure also works with TE polarized light, in contrary to the SPR method. Using azimuthally polarized illumination, one can generate confined and enhanced evanescent Bessel beam with a donut shape. This kind of beam would have applications such as particle trapping and manipulations.

Application to an Apertureless Near-Field Scanning Optical Microscopy (NSOM)

Simulation of Field Enhancement

With the capabilities of exciting cylindrically polarized mode in fiber, an apertureless NSOM can be fabricated that maintains the architecture of conventional NSOM while eliminating the aperture. Meanwhile, it provides strong field enhancement effect as well as high spatial-resolution similar to the apertureless metallic tip NSOM. As a radially polarized $TM_{01}$ mode propagates in the fiber and approaches the tapered tip end, the mode will pass the cutoff point and become evanescent. Surface plasmon waves are excited and propagate to the tip end. One intriguing property of the surface plasmon is its strong field enhancement effect. The excitation of surface plasmons is associated with TM polarized light that has electrical field that lies in the plane of incidence. When a radially polarized mode is launched into a metallic coated optical fiber tip, the whole beam is TM polarized with respect to the dielectric/metal interface of the fiber, providing a very efficient way to generate surface plasmon. The radial symmetry of the configuration leads to a constructive interference of these surface plasmons, creating an extremely strong localized field near the tip. This strong localized field is then used as a high spatial resolution probe.

This field enhancement effect has been verified with numerical modeling with COMSOL multiphysics, a finite-element-method (FEM) software. FIG. 15 shows the FEM simulated results for one fully metalized tip under radial polarized illumination. The top plots show the two-dimensional cross sectional, three-dimensional sliced and three-dimensional mesh plot of the field distribution. It can be seen that a strong and localized field appears at the tip apex. The bottom plot shows the line scan at 10 nm from the tip apex. FWHM less than 10 nm can be obtained. The core of tip is assumed to be silica with index of 1.5. The tip can be totally metalized with a silver coating of 40 nm. The silver coating on the tip can have a thickness of about 30 nm to about 100 nm. The tip end has a radius of 5 nm. A radially polarized beam with 633 nm wavelength is used for the simulation. It was found that a field enhancement factor of more than 250 can be obtained in such a tip design. The intensity will be enhanced by 62500 times. The field distribution at 10 nm away from the tip apex has a full-width-half-maximum (FWHM) of 10 nm. From the simulations, it was found that the enhancement factor strongly depends on the geometry of the tip and illumination. For example, the enhancement depends on the tip apex angle, the length of the tip and the size of radially polarized beam at the entrance to the tip. In some cases, field enhancement of several hundreds can be obtained, while in other cases, field enhancement of just about 1 could result as well. However, with radial polarization, there is always a field enhancement. A simple way to optimize the enhancement is through adjustment of the illumination size at the entrance to the tip. This can be done with inserting an iris in the illumination path and adjusting the effective NA of the illumination optics.

In the above simulations, a radial polarization was used. In another embodiment, circularly polarized vortex beams with appropriate combinations of handness and topological charge can be used as a simpler alternative to generate the same surface plasmon and field enhancement effect. The correct combination can be achieved by rotating a quarter-wave plated after a linear polarizer or flipping the SPE orientation. In this case, the field enhancement factors will be approximately 50% of the case when radial polarization is used. However, the setup using circularly polarized vortex beam is much simpler and easy to operate.

Tuning Fork Based Apertureless NSOM System

One can construct an apertureless NSOM using standard tuning fork shear force feedback. The apertureless NSOM design is illustrated in FIG. 16. A halogen bulb and a CCD camera are attached for large field of view imaging. The apertureless NSOM tip are shown in the inset. No opening of the metallic coating is required. Although a transmission mode is illustrated, reflection mode can also be realized easily. The instrument is grouped into a CV beam generation block, an inverted optical microscope block and a signal detection block. The CV beam generation block converts the laser output into radial polarization. The apertureless NSOM block couples the radially polarized beam into an optical fiber with metal-coated tapered apertureless tip. The tip approaches the sample using shear-force tuning-fork feedback. Transmitted signal is collected by the infinity corrected oil immersion objective lens of the inverted microscope and sent to the detection block. The inverted microscope block is needed to aid sample positioning and multiple light path illumination and detection. The tuning fork and the apertureless tip are mounted on a scanning head with XYZ piezo scanner and dithering piezo (see FIG. 16). Topographic information is obtained from the z-piezo voltage and the tuning-fork feedback. High resolution images are obtained through raster scanning. A low profile nano positioner is mounted on the stage of the inverted microscope for sample scanning. For sample scanning, the XYZ scan can be de-coupled. The scanning head with a z-piezo will be responsible for generating the topography. The sample will be mounted on a XY scanner which will be responsible for two-dimensional mapping. The output from the CV beam generation block can also be coupled into one illumination port of the inverted microscope and focused by the oil immersion lens into the sample for other applications. Various types of detectors including a photomultiplier tube (PMT), a single photon counting avalanche photodiode detector (APD), as well as a TE cooled charge coupled device (CCD) array detector are used in combination with an imaging spectrometer. The output from the PMT/APD is connected to a photon counting system. The CCD array is used for fast spectrum acquisitions and imaging. The laser beam may be chopped and lock-in detection can be used for noise rejection. A halogen bulb source and CCD camera are also attached to the inverted microscope for large field of view observation and recording.

The metallic coated apertureless fiber can be mounted to a tuning fork. A dithering piezo is used to mechanically drive the tuning fork. The motion of the tuning fork is monitored by the piezoelectric current generated by the stress induced in the quartz. The tip-sample distance is regulated by monitoring the resonant phase or amplitude changes that are induced by the tip-sample interactions. Both normal force and shearing force detection with tuning fork have been reported. In this apertureless NSOM, shear force mode is used. The use of tuning fork for force detection eliminates the needs for an extra laser source and the tedious alignment procedure before taking images. The signal can be collected either in reflection mode (the collection optics will be on the same side of illumination with respect to the sample) or in transmission mode (if the sample is transparent to the desired signal). An inverted microscope can be used for the sample positioning and optical signal collection. It has multiple optical input/output ports to facilitate different laser sources and detection. It also features stray light rejecting optical design and vibration-free mechanical design, which are critical for achieving high signal-to-noise ratio sub-50 nm resolution of the NSOM.

However, sophisticated illumination geometry is required to excite the localized mode on the tip. The efficiency strongly depends on the polarization of the illumination, demanding extremely careful alignment of the illumination. Compared with existing NSOM techniques, the proposed apertureless NSOM has the following advantages: 1) Maintains the simple architecture of an aperture NSOM, 2) Eliminates the delicate aperture opening requirement, 3) Improve the spatial-resolution of NSOM by nearly an order of magnitude, 4) Offers local field enhancement comparable with metallic tip apertureless NSOM, and 5) Avoids sophisticated alignment required in the apertureless metallic tip NSOM.

Cantilever/Tuning Fork Hybrid Apertureless NSOM

One of the drawbacks that hampered wider applications of fiber tip based NSOM is the delicacy and fragility of the optical fiber tip itself, demanding experienced personnel and extremely careful handling. In contrary, atomic force microscope (AFM) probes are more rigid and the tip radius can be made extremely small. Apertureless NSOM using metalized AFM tips has demonstrated excellent spatial resolution and good field enhancement effects. However, in order to achieve the optimal field enhancement, the polarization of focused laser beam needs to be parallel to the tip. This requires either a side illumination or a slight displacement of the tip from the center of focus. Extremely careful alignment of the focused laser spot and the tip is required. In addition, in order to regulate the tip-sample distance and generate topographical images, typically a laser beam is aligned on the cantilever and reflected onto a position sensitive detector. The alignment of the laser beam is often time very tedious and significantly affects the sensitivity and quality of the images. Thus the operation of these apertureless NSOMs is very time consuming and the results are strongly experience dependant.

A cantilever based tuning fork normal force apertureless NSOM using highly focused radial polarization to solve this conundrum is presented. The design is illustrated in FIG. 17. A metal coated AFM probe is glued to one prong of a 100 kHz tuning fork sensor. The attachment of the AFM probe creates a mass asymmetry between the two prongs that is necessary for the desired anti-symmetric resonant mode. The tip-sample distance is regulated by monitoring the amplitude or the phase lag of the tuning fork feedback signal. The tuning fork feedback eliminates the tedious laser diode to cantilever alignment, enabling more user friendly and experience independent operation. The tip of the metalized AFM probe is illuminated by a strongly focused radial polarization from the inverted microscope (FIG. 16). The use of radial polarization creates an extremely strong longitudinal field that is parallel to the tip, which is critical for field enhancement in apertureless NSOM. As comparison, the longitudinal components of both focused linear polarization and radial polarization are calculated and compared. Both polarizations carry the same power and are focused under the same condition. Radial polarization provides at least four times stronger longitudinal component that is responsible for the field enhancement effect. Extremely high signal-to-noise ratio (SNR) improvement can be obtained in non-linear optical spectroscopy. In contrary to linear polarization, the longitudinal component of focused radial polarization peaks at the center of the focus. Thus, aligning the tip with the excitation field becomes much easier than previous tip-enhanced apertureless NSOM.

In another mode of operation, the strongly focused radial polarization can illuminate the metallized AFM probe from the top. For most of the Si or SiN based AFM probes, one needs to choose a wavelength where these materials are transparent. These wavelengths will be in the near infrared. One can simply coat the AFM probes that are available on the market with metals that can support SPR (such as Silver, Gold, and Aluminum etc). When the radial polarized beam is coupled into the tip, a strong field will be generated at the tip apex which can be used as apertureless NSOM probe. This provides a simple way of making an apertureless NSOM probe. In addition, it is possible to fabricate a micro-lens on the AFM probe cantilever to improve the coupling efficiency (FIG. 18).

Compared with existing NSOM techniques, the proposed apertureless NSOM has the following significant advantages: 1) More rigid tip, 2) User friendly and easy operation by eliminating sophisticated alignment requirements, 3) Improves the spatial-resolution of NSOM to better than 10 nm and 4) Offers highest local field enhancement, and consequently, faster image acquisition.

Cantilever Based Apertureless NSOM System

In order to overcome the drawback of low throughput, cantilever based nano-aperture probes have been developed for NSOM. Typically, these probes are compatible with AFM/scanning probe microscope (SPM) platforms. One can convert these cantilever based aperture NSOM into an apertureless NSOM using the radial polarization. In order to modify these aperture NSOM, one need to change the illumination to radial polarization (or circularly polarized vortex beam) and change the probe to fully metalized apertureless probes. The apertureless probes can be made from these cantilever based aperture probe by fully metallization. Or one can use the apertureless probes described in the previous section. This will provide an economic way of developing an apertureless NSOM while keeping it original functions as aperture NSOM and/or AFM, making it a truly versatile and multi-function tool.

Nano-Raman Using Apertureless NSOM

A nano-Raman system can be built by combining the apertureless NSOM described in previous sections with Raman spectroscopy. Due to the strong field enhancement and extremely high resolution, reliable Raman spectrum from very localized region can be obtained. One example diagram for such nano-Raman system is shown in FIG. 19. Raman spectroscopy system will be attached to the apertureless NSOM system and information about structural properties as well as chemical compositions of sample can be analyzed by study the features of the Raman spectrum. Combined with the apertureless NSOM techniques, Raman spectrum from an extremely confined region of sample can be acquired and analyzed. This nano-Raman probe is a promising tool for identifying and analyzing spatially resolved micromechanical properties and chemical compositions of materials, thus providing comprehensive nanocharacterization of the topographical, micromechanical, and microchemical properties of materials with spatial resolution below 10 nm.

Scanning probe microscope (SPM) such as AFM and NSOM can be used in combination with Raman spectroscopy to further improve spatial resolution into nanometer range. Besides a much high spatial resolution, nano-Raman spectroscopy has fundamental difference compared with the micro-Raman and conventional Raman spectroscopy. Due to a large field gradient in the vicinity of the scanning probe, nano-Raman spectroscopy provides much more information than micro-Raman techniques.

In addition, the Raman signal can be further improved if the Raman signal is collected through tranmission mode. If we consider the Raman signal comes from a dipole radiation, it is well known that dipole radiation near or at an interface will coupled strongly to the high index substrate. Thus a major portion of the Raman signals is not collected and detected with a reflection mode detection. This portion of the signal can not be detected simply with a transmission mode, since those photons are beyond the total internal reflection angle and will not emit from the back side without modifications. However, techniques that have been developed for solid immersion lens and subsurface imaging can used to collect these "lost" photons. Using these techniques, significantly improved the Raman signal strength and the collection efficiency. Essentially, one can use a lens cap that matched the index of the substrate. The lens cap is designed such that the lens cap and the substrate forms a hemispherical lens or a super SIL. Then those "lost" photons can be coupled out the substrate and reach the detector. One of such design is illustrated in FIG. 19. In FIG. 19, circularly polarized vortex (CPV) beam is used as the illumination to excited strongly localized surface plasmon. The spiral phase element (SPE), quarter-wave plate, and polarizer are mounted on rotational stages. The orientations of the polarizer and quarter wave plate are set up to generate circular polarization. The SPE is oriented such that a strong longitudinal component can be generated when the CPV beam is focused. A transmission mode is illustrated. Reflection mode is also illustrated with dash lines in the diagram. The signal processing unit processed both the electronic control feedback and the Raman spectroscopy data. The iris in the illumination path is adjustable to produce the optimized enhancement effect at the tip apex. The probe can be made of different materials, depending on the laser wavelength and whether reflection or transmission mode will be used. The probe materials should be transparent to the illumination wavelength. The probe is fully coated with metal (silver, gold or aluminum etc.) thin film. A solid immersion lens cap that matched the index of the sample substrate to further improve the signal strength and collection efficiency is also shown with dashed lines. This is another significant improvement of the nano-Raman for reliable spectroscopy analysis. One example application will be for samples with silicon substrates. In this case, one may use a near infrared (NIR) excitation such as 1.06 micron wavelength. Then the Raman bands will be transparent to the substrate and can be collected using the proposed lens cap techniques to improve the signal. Other wavelength can also be used as long as the interested Raman bands are transparent to the sample.

The apertureless NSOM and the nano-Raman system described above have numerous applications in semiconductor manufacturing, materials research and development, biological sciences and many other research areas that require high resolution optical imaging. The strong field enhancement arising from the radial polarization symmetry and surface plasmon excitation further opens the doors to many linear and nonlinear (such as second harmonic imaging, third harmonics imaging etc.) optical imaging with nanoscale resolution. These new imaging capabilities certainly will benefit many other research areas and applications that are beyond the scopes mentioned above. In addition, the focusing properties of the CV beams as well as circularly polarized vortex beams with have applications in nano-particle trapping, manipulation as well as high resolution imaging. The following provides some of the examples of the potential applications of the tools described above.

From optical microscope for visual inspection, white light interferometer for surface analysis, to spectroscopic ellipsometer for complex thin films characterization, optical metrology techniques have been powerful tools and widely used in the semicondcutor fabrication lines. However, the tremendous advances in nanolithography and micro-fabrication severely stretches the capabilities of optical metrology techniques. According to the International Technology Roadmap for Semiconductors (ITRS), one of the key metrology areas for the 45 nm node and beyond that urgently requires a solution in the next several years is structural and elemental analysis at devices dimensions. "Materials characterization and metrology methods are needed for control of interfacial layers, dopant positions and atomic concentrations relative to device dimensions." The nano-Raman system described in previous section is a very promising solution to these technical challenges. Materials micromechanical properties, local deformations, and compositions affect the Raman shift. Thus, measuring the Raman shift image can provide structural (stress/strain) and elemental information about the sample. With resolution better than 10 nm, our nano-Raman system may provide a viable solution to the device level structural and elemental metrology for the semiconductor industry. With the maturing NSOM techniques, the apertureless NSOM and nano-Raman may be integrated in the semiconductor fabrication line for in-line metrology and improving the yield.

Due to their unique mechanical, thermal, electrical, optical properties and quantum confinement effects, carbon nano tubes (CNTs) have been intensively studied since their discovery in the earlier 1990s. Among their optical properties, Raman "signatures" are often used to characterize single wall carbon nano tubes (SWCNTs). Raman spectroscopy has been a powerful tool for the investigation of molecular vibrations and rotations. Specific molecules have their own distinctive features or "fingerprints" in the spectrum shifts. Through studying the Raman shift, a whealth of information about the sample can be obtained. For SWCNTs, several different modes of Raman spectrum have been indentified and associated with different properties of them. For examples, the so-called radial breathing mode (RBM, ~100-300 wavenumbers) can be used to characterize the tube diameter, chirality, structure and conductivity (metallic or semiconducting); the D band (~1300 wavenumbers) can be used to characterize for defects. Most spectroscopy research of SWCNTs are ensemble averaged measurements due to lack of resolving power. Recently, successful nano scale Raman of individual SWCNT with tip-enhanced NSOM has been reported [35]. Realization of reliable nano-Raman measurements is considered as the "holy grail" in the Raman spectroscopy community. With the strong field enhancement of our new apertureless NSOM, the Raman signal is significantly strengthened, enabling reliable comprehensive characterization of the SWCNTs. In addition, it has been reported that the near-field Raman spectroscopy could have distictive different features than that of far-field Raman spectroscopy [36]. This is due to the selection rule changes caused by the strong field gradient near the tip apex. However, such a difference has not been observed in Raman studies of SWCNTs. With the described NSOM technique, it may be possible to explore the plasmonic properties of the CNTs. his may open opportunities for many potential applications of CNTs in sensors and photonic/plasmonic circuitry.

In addition to the function of compartmentalizing the cell, cell membranes are also involved in many critical processes such as metabolism, signaling and cellular trafficking. In addition, many lipid metabolites have been found to act as local mediators of physiological events related to inflammation, reproduction, regulation of the sleep-wake cycle, and aging. Understanding the intra-membrane interactions involved in these cellular processes allows for fundamentally new opportunities to combat a variety of human diseases. A particular aspect of membrane biology that has received much attention is the arachidonic acid cascade. Metabolism of polyunsaturated arachidonic acid (3) results in the production of many potent local mediators with farranging physiological effects. Many of these metabolites are known to be involved in the inflammation response. However, much less is known about the isoprostanes that are produced via a nonenzyme catalyzed oxidation of membrane-bound arachidonic acid. Besides of serving as reliable indicators of oxidant stress, many isoprostanes have exhibited potent biological activities related to inflammatory events. The proposed polarization enhanced microscopy techniques opens tremendous opportunities to bring new spectroscopic techniques to identify and study interactions and functions of those lipid oxidation products with unprecedented spatial resolution and sensitivity. These techniques are ideally suitable for membrane and intra-membrane studies. Florescence labels such as Cy5 and BODIPY R6G succinimidyl ester can be used to probe the membrane interactions of these lipid metabolites. Gold nano-particles and Raman spectroscopy may also be applied for label free detections of these interactions. The active labeled isoprostanyl phospholipid can be used to probe the metabolite's location, lifetime, distribution, as well as associations within the two dimensional constraints of the cellular membrane. Potentially, information at the single-molecule level may be achievable with the apertureless NSOM, surface plasmon microscope, as well as the laser trapping NSOM. In addition, insight into the changes in the biophysical properties of the membrane may be also uncovered with these techniques.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Recitations herein of a component of the present invention being "configured" in a particular way or to embody a particular property or function, are structural recitations as opposed to recitations of intended use. For example, references herein to a beam generating assembly and an inverted optical microscope assembly being "configured" to convert a laser beam in a particular manner denotes an existing physical condition of the beam generating assembly and the inverted optical microscope assembly and, as such, is to be taken as a definite recitation of structural characteristics.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. An optical system comprising a beam generating assembly, an optical microscope assembly, and a signal detection assembly, wherein:
the beam generating assembly comprises a laser source and is configured to convert laser output from the laser source into a polarized cylindrical vector beam or a circularly polarized vortex beam as input to the optical microscope assembly;
the optical microscope assembly comprises a plasmon-generating optical probe set-up and an objective lens;
the beam generating assembly is configured to direct the polarized beam into the plasmon-generating optical probe set-up of the optical microscope assembly;
the plasmon-generating optical probe set-up comprises a metal coated, tapered, apertureless tip defining an apex;
the apertureless tip is configured to excite surface plasmon waves and direct the surface plasmon waves to the apex of the tip when the polarized beam propagates from the beam generating assembly in the direction of the apex of the tip; and
the objective lens is configured to collect near field optical signals from a sample positioned adjacent to the apex of the apertureless tip and direct the near field optical signals to the signal detection assembly.

2. The system of claim 1, wherein the signal detection assembly comprises a spectrometer or a photon counting system.

3. The system of claim 2, wherein:
the system further comprises a device for image processing and display; and
the signal detection assembly is configured to send an output to the device for imaging processing and display.

4. The system of claim 1, wherein the signal detection assembly comprises at least one component selected from one group consisting of a photomultiplier tube, a single photon counting avalanche photodiode, a charged-coupled device (CCD) array detector, a spectrometer, a CCD-spectrometer, and combinations thereof.

5. The system of claim 1, wherein the optical microscope assembly further comprises a halogen bulb source and a camera for large field of view observation and recording.

6. The system of claim 1, wherein the metal-coated tapered apertureless tip is coated with layer of silver with a thickness of between about 30 nm to about 100 nm.

7. The system of claim 1, wherein the geometry of the metal-coated tapered apertureless tip is configured to influence the field enhancement factor of the optical system.

8. The system of claim 1, wherein the metal-coated tapered apertureless tip is configured to be mounted onto a tuning fork, driven by a dithering piezo.

9. The system of claim 8, wherein the optical microscope assembly is configured to approach the sample using shear-force tuning-fork feedback.

10. The system of claim 8, wherein topographic information of the sample is obtained from the z-piezo voltage and the tuning fork feedback.

11. The system of claim 8, wherein metal-coated tapered apertureless tip is an atomic force microscope probe.

12. The system of claim 11, wherein the distance between the metal-coated tapered apertureless tip and the sample is configured to be regulated by monitoring the amplitude of the tuning fork feedback.

13. The system of claim 1, wherein the optical microscope assembly further comprises a low profile nano positioner for sample scanning.

14. The system of claim 1, wherein the objective lens is an infinity-corrected immersion lens.

15. The system of claim 1, wherein the optical microscope assembly further comprises a Raman spectroscopy system configured to collect Raman signals in transmission or in reflection mode.

16. The system of claim 15, wherein the signal detection assembly is configured to process Raman spectroscopy data.

17. The system of claim 1, wherein the beam generating assembly is configured to convert laser output from the laser source into a polarized cylindrical vector beam.

18. The system of claim 1, wherein the tip is a tapered optical fiber tip and the polarized beam propagating from the beam generating assembly is injected into the tapered optical fiber tip.

19. The system of claim 1, wherein the beam generating assembly is configured to convert laser output from the laser source into a circularly polarized vortex beam.

* * * * *